United States Patent
Dhanasekharan

(10) Patent No.: US 9,441,196 B2
(45) Date of Patent: Sep. 13, 2016

(54) DEVICE FOR VIRAL INACTIVATION OF LIQUID MEDIA

(75) Inventor: Muthukumar Dhanasekharan, Shrewsbury, MA (US)

(73) Assignee: Genzyme Corporation, Cambridge, MA (US)

( * ) Notice: Subject to any disclaimer, the term of this patent is extended or adjusted under 35 U.S.C. 154(b) by 699 days.

(21) Appl. No.: 13/702,355

(22) PCT Filed: Jun. 6, 2011

(86) PCT No.: PCT/US2011/039301
§ 371 (c)(1),
(2), (4) Date: Dec. 6, 2012

(87) PCT Pub. No.: WO2011/156281
PCT Pub. Date: Dec. 15, 2011

(65) Prior Publication Data
US 2013/0078702 A1    Mar. 28, 2013

Related U.S. Application Data

(60) Provisional application No. 61/352,276, filed on Jun. 7, 2010.

(51) Int. Cl.
*A61L 2/00* (2006.01)
*C12M 1/00* (2006.01)
(Continued)

(52) U.S. Cl.
CPC .............. *C12M 47/00* (2013.01); *A61L 2/0047* (2013.01); *C02F 1/325* (2013.01); *C12N 13/00* (2013.01);
(Continued)

(58) Field of Classification Search
CPC ... A61L 2/0047; A61L 2/10; A61L 2202/10; A61L 2202/11; A61L 2202/21; C02F 1/325; C02F 2201/3223; C02F 2201/3226; C02F 2201/3227; C02F 2201/3228; C02F 2301/026; C02F 2201/328; C02F 2301/024; C12N 13/00; C12M 47/00
See application file for complete search history.

(56) References Cited

U.S. PATENT DOCUMENTS

2002/0096648 A1    7/2002    Kaiser et al.
2003/0052278 A1*   3/2003    Duarte ......................... 250/438
(Continued)

FOREIGN PATENT DOCUMENTS

DE    36 24 169 A1    1/1987
DE    39 24 349 A1    1/1991
(Continued)

OTHER PUBLICATIONS

International Search Report, PCT/US2011/039301, dated Sep. 9, 2011, 5 pages.
International Preliminary Report on Patentability, PCT/US2011/039301, dated Dec. 10, 2012, 8 pages.
(Continued)

*Primary Examiner* — Timothy Cleveland
(74) *Attorney, Agent, or Firm* — Lathrop & Gage LLP; James H. Velema, Esq.

(57) ABSTRACT

An apparatus (100) capable of viral inactivation of liquid media includes at least one coaxial cylinder (110) constructed of an outer cylinder (120) and an inner cylinder (130), a liquid media inlet (140), at least one emitter of type C ultraviolet radiation (145), and a liquid media outlet (150). The inner cylinder has an outer diameter adapted to form a gap (160) between the outer diameter of the inner cylinder and the inner diameter of the outer cylinder. The media flows in a substantially cyclonic flow path along the gap. The at least one emitter of type C ultraviolet radiation is placed inside the inner cylinder. The outlet is connected to the outer cylinder at, or proximal to, an end of the outer cylinder opposite the inlet.

32 Claims, 42 Drawing Sheets

(51) Int. Cl.
*C02F 1/32* (2006.01)
*C12N 13/00* (2006.01)

(52) U.S. Cl.
CPC ...... *A61L 2202/21* (2013.01); *C02F 2201/328* (2013.01); *C02F 2201/3227* (2013.01); *C02F 2301/024* (2013.01); *C02F 2301/026* (2013.01)

(56) References Cited

U.S. PATENT DOCUMENTS

2007/0003430 A1 1/2007 Kaiser et al.
2008/0095661 A1 4/2008 Kohler et al.

FOREIGN PATENT DOCUMENTS

| EP | 0 202 820 A2 | 11/1986 |
| EP | 0 803 472 A1 | 10/1997 |
| WO | WO9515294 A1 | 6/1995 |
| WO | WO2006073409 A1 | 7/2006 |

OTHER PUBLICATIONS

SteriBeamSystems (2011) "Sterilization with UV Flash Lamps" SteriBeamSystems GmbH. Available on the Internet at URL: http://www.steribeam.com/technology/SBS-PUV-principles.pdf. [Retrieved from Internet on Aug. 21, 2015].

* cited by examiner

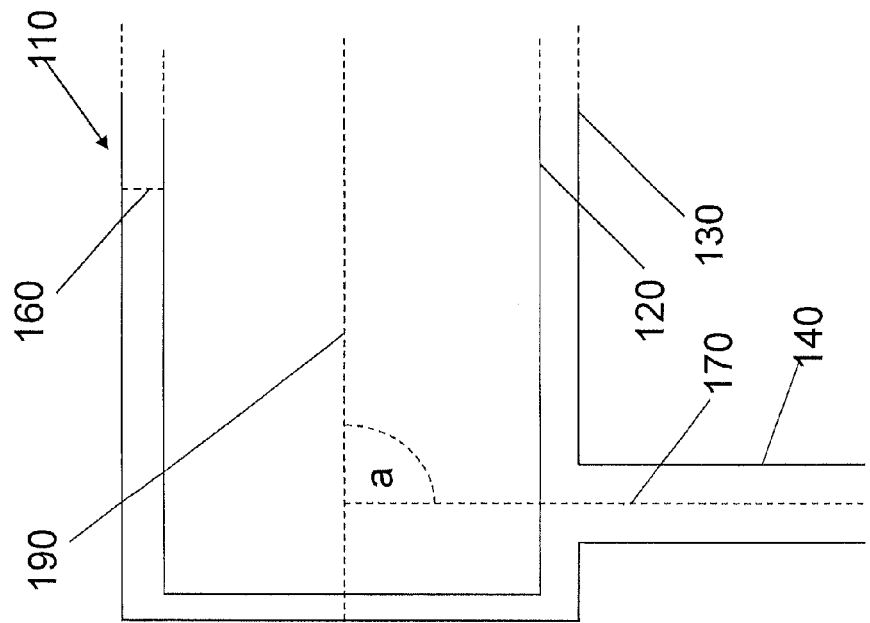
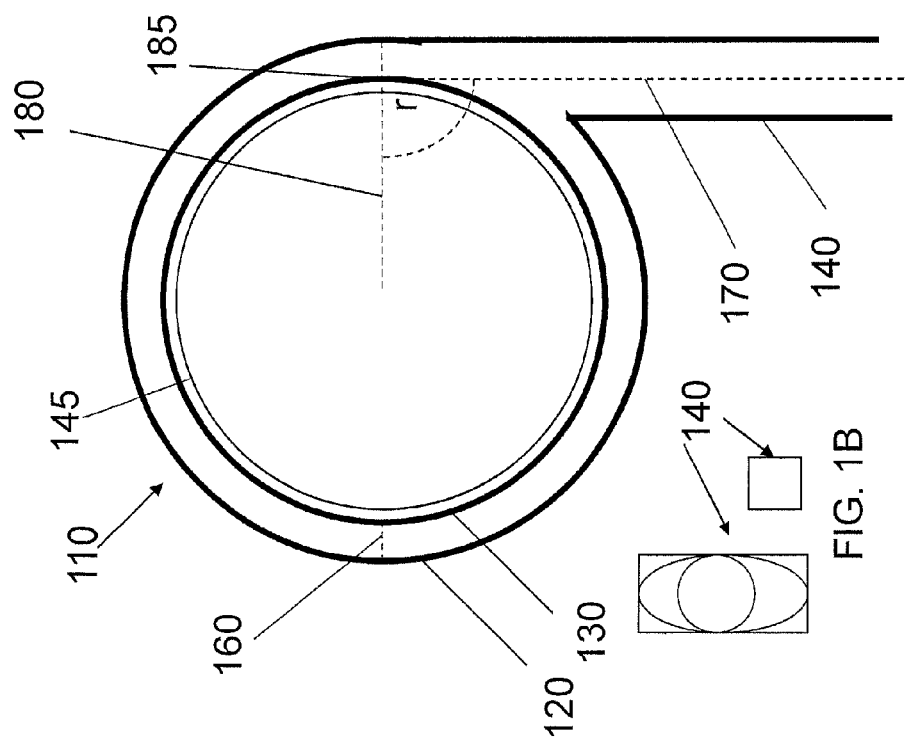
FIG. 1C
FIG. 1B

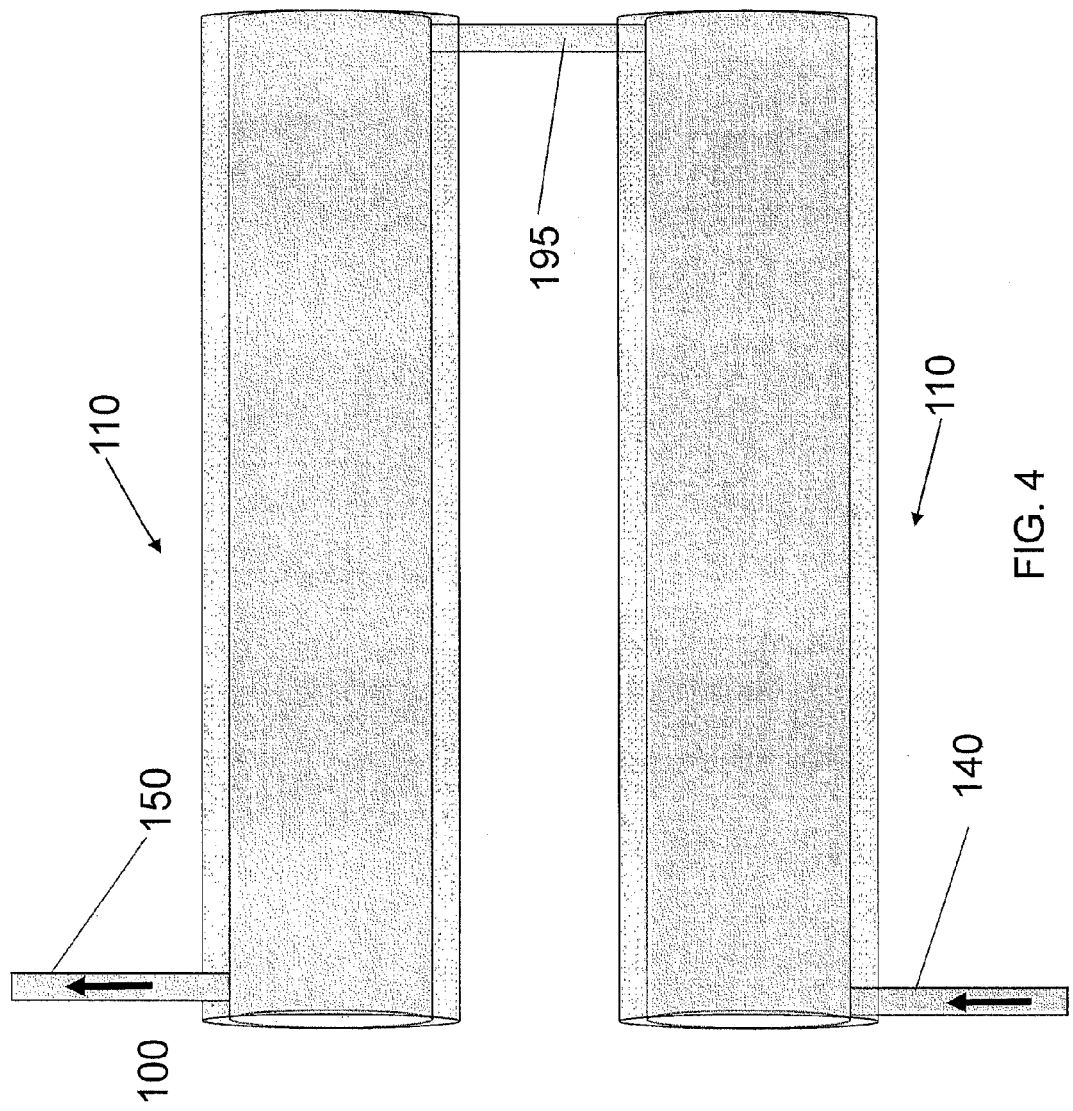

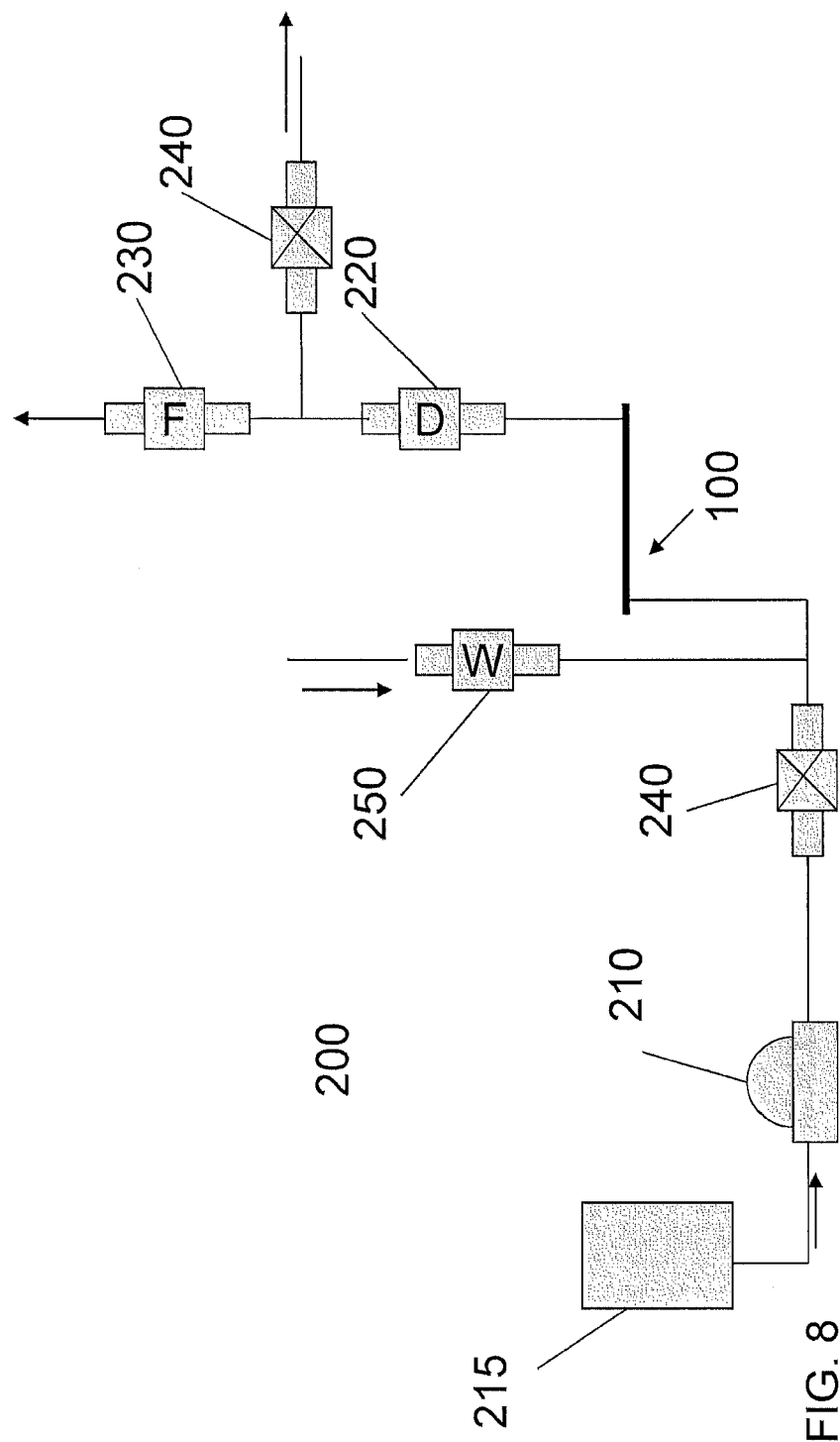

DEVICE FOR VIRAL INACTIVATION OF LIQUID MEDIA

RELATED APPLICATIONS

This application is a 35 U.S.C. §371 filing of International Application No. PCT/US2011/039301 filed Jun. 6, 2011, which claims priority to U.S. Provisional Application No. 61/352,276, filed on Jun. 7, 2010. The entire contents of each of the above documents are incorporated herein by reference.

BACKGROUND OF THE INVENTION

Viral mitigation throughout all phases of biopharmaceutical manufacturing processes is an increasingly strict requirement established by international or national regulatory bodies in order to prevent viral contaminants in the application of biopharmaceuticals for therapeutic or non-therapeutic purposes. Several methods have been employed to inactivate and/or remove large or small, enveloped or non-enveloped viral particles from biopharmaceutical product compositions. Examples of such methods include filtration (e.g., 20 nm filtration, Q membrane chromatography, depth filter technology), heat (e.g., high temperature short time (HTST) pasteurization), chemical (e.g., addition of solvents—detergents or chemical agents), or radiation (e.g., ultraviolet or gamma-ray irradiation). These methods have been used primarily downstream in the biopharmaceutical manufacturing process due to their low throughput and/or high cost. Viral inactivation of cell culture media input into a biopharmaceutical manufacturing process, where up to 20,000 L or more are processed per day, would be prohibitive in terms of time and cost with existing methods. Some methods, such as ultraviolet C (UVC) irradiation, are challenging to apply to biopharmaceutical manufacturing processes, because, unlike in, for example, water treatment, over-exposure of the media (particularly media containing serum) can be detrimental, and therefore the radiation dose needs to be delivered uniformly to the media and controlled to within a relatively narrow range. An additional challenge for ultraviolet irradiation of media, particularly media containing serum, is that the UV transmittance in the UVC range (e.g., at 254 nm) of the media is substantially lower than the UV transmittance of, for example, water, in this wavelength range. In addition, it is desirable that devices used in high throughput biopharmaceutical manufacturing contain components that are amenable to cleaning and sterilization (e.g., clean-in-place (CIP) and steam-in-place (SIP) procedures). Therefore, there is a need for methods and apparatuses which enable high throughput viral inactivation of low transmittance liquid media for biopharmaceutical and other applications.

SUMMARY OF THE INVENTION

The invention generally is directed to methods and apparatuses which enable high throughput viral inactivation of liquid media.

In one embodiment, an apparatus capable of viral inactivation of a high absorbance liquid media includes at least one coaxial cylinder constructed of an outer cylinder (with dimensions of length, inner diameter, and outer diameter) and an inner cylinder coaxial with the outer cylinder. The apparatus further includes a media inlet, at least one emitter of type C ultraviolet radiation, and a media outlet. The inner cylinder has a length substantially equal to the length of the outer cylinder and an outer diameter adapted to form a gap between the outer diameter of the inner cylinder and the inner diameter of the outer cylinder. The liquid media flows in a substantially cyclonic flow path along the gap. The media inlet is connected to the outer cylinder at, or proximal to, an end of the outer cylinder. The inlet is configured to flow the media along the substantially cyclonic flow path along the gap. The at least one emitter of type C ultraviolet radiation is placed inside the inner cylinder so as to emit the type C ultraviolet radiation towards the media to be treated with the type C ultraviolet radiation and thereby inactivate viruses in the media. The outlet is connected to the outer cylinder at, or proximal to, an end of the outer cylinder opposite the inlet. In a further embodiment, the media to be treated is a cell culture media. In yet a further embodiment, the media to be treated contains serum.

In another embodiment, a method of inactivating viruses in a high absorbance liquid media includes introducing the liquid media into at least one coaxial cylinder that includes a gap along the length of the cylinder between the outer diameter of an inner cylinder and the inner diameter of an outer cylinder. The media is introduced through an inlet configured to flow the liquid media along a substantially cyclonic flow path along the gap. The method further includes irradiating the media with at least one emitter of type C ultraviolet radiation placed inside the inner cylinder so as to emit the type C ultraviolet radiation towards the liquid media to thereby inactivate viruses in the media. The method then includes flowing the media through a media outlet connected to the outer cylinder proximal to an end of the outer cylinder opposite the inlet. In a further embodiment, the media to be treated is a cell culture media. In yet a further embodiment, the media to be treated contains serum.

This invention has many advantages, such as high throughput viral inactivation of liquid media for biopharmaceutical processes, and amenability to cleaning procedures (e.g., clean-in-place (CIP) and steam-in-place (SIP)). Another advantage of the apparatuses of the invention is the flexibility in the configurations, which enable them to be fitted to restricted or customized space requirements.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1B is a schematic illustration of cross sections of the inlet and coaxial cylinder of the apparatus shown in FIG. 1A.

FIG. 1C is a schematic illustration of a side view of the inlet and coaxial cylinder of the apparatus shown in FIG. 1A.

FIG. 4 is a schematic illustration of a side view of an apparatus for viral inactivation of cell culture media according to this invention with two vertically stacked coaxial cylinders.

FIG. 8 is a schematic illustration of a plan view of an apparatus for viral inactivation of cell culture media according to this invention; W=wash/flush valve, F=flow control valve, D=dose meter.

FIGS. 25A, 25B, and 25C are graphs of UV dose distributions in cell culture media through the UVC reactor as a function of fluorescence distribution for: FIG. 25A-1 flow rate=2.75 lpm, predicted mean UV dose=91 mJ/cm$^2$; FIG. 25A-2 experimental mean UV dose=82 mJ/cm$^2$; FIG. 25B-1 flow rate=4.75 lpm, predicted mean UV dose=53 mJ/cm$^2$; FIG. 25B-2 experimental mean UV dose=52 mJ/cm$^2$; FIG. 25C-1 flow rate=7.6 lpm, predicted mean UV dose=35 mJ/cm$^2$; FIG. 25C-2 experimental mean UV dose=50 mJ/cm$^2$.

FIGS. 26A, 26B, and 26C are graphs of UV dose distributions of 10% DBS in cell culture media through the UVC reactor as a function of fluorescence distribution for: FIG. 26A-1 flow rate=2.2 lpm, predicted mean UV dose=89 mJ/cm$^2$; FIG. 26A-2 experimental mean UV dose=47 mJ/cm$^2$; FIG. 26B-1 flow rate=3.8 lpm, predicted mean UV dose=53 mJ/cm$^2$; FIG. 26B-2 experimental mean UV dose=36 mJ/cm$^2$; FIG. 26C-1 flow rate=6 lpm, predicted mean UV dose=34 mJ/cm$^2$; FIG. 26C-2 experimental mean UV dose=28 mJ/cm$^2$.

FIGS. 28A and 28B are graphs of UV dose distributions of 0.1 g/L (absorbance of 4.7 absorbance units) Vitamin C solution through the UVC reactor as a function of fluorescence distribution for: FIG. 28A-1 flow rate=2.2 lpm, predicted mean UV dose=104 mJ/cm$^2$; FIG. 28A-2 experimental mean UV dose=81 mJ/cm$^2$; FIG. 28B-1 flow rate=3.8 lpm, predicted mean UV dose=61 mJ/cm$^2$; FIG. 28B-2 experimental mean UV dose=63 mJ/cm$^2$.

FIGS. 29A, 29B, and 29C are graphs of UV dose distributions of 0.04 g/L (absorbance of 1.94 absorbance units) Vitamin C solution through the UVC reactor as a function of fluorescence distribution for: FIG. 29A-1 flow rate=2.75 lpm, predicted mean UV dose=91 mJ/cm$^2$; FIG. 29A-2 experimental mean UV dose=81 mJ/cm$^2$; FIG. 29B-1 flow rate=4.75 lpm, predicted mean UV dose=53 mJ/cm$^2$; FIG. 29B-2 experimental mean UV dose=60 mJ/cm$^2$; FIG. 29C-1 flow rate=7.6 lpm, predicted mean UV dose=35 mJ/cm$^2$; FIG. 29C-2 experimental mean UV dose=47 mJ/cm$^2$.

DETAILED DESCRIPTION OF THE INVENTION

Figure 1A:
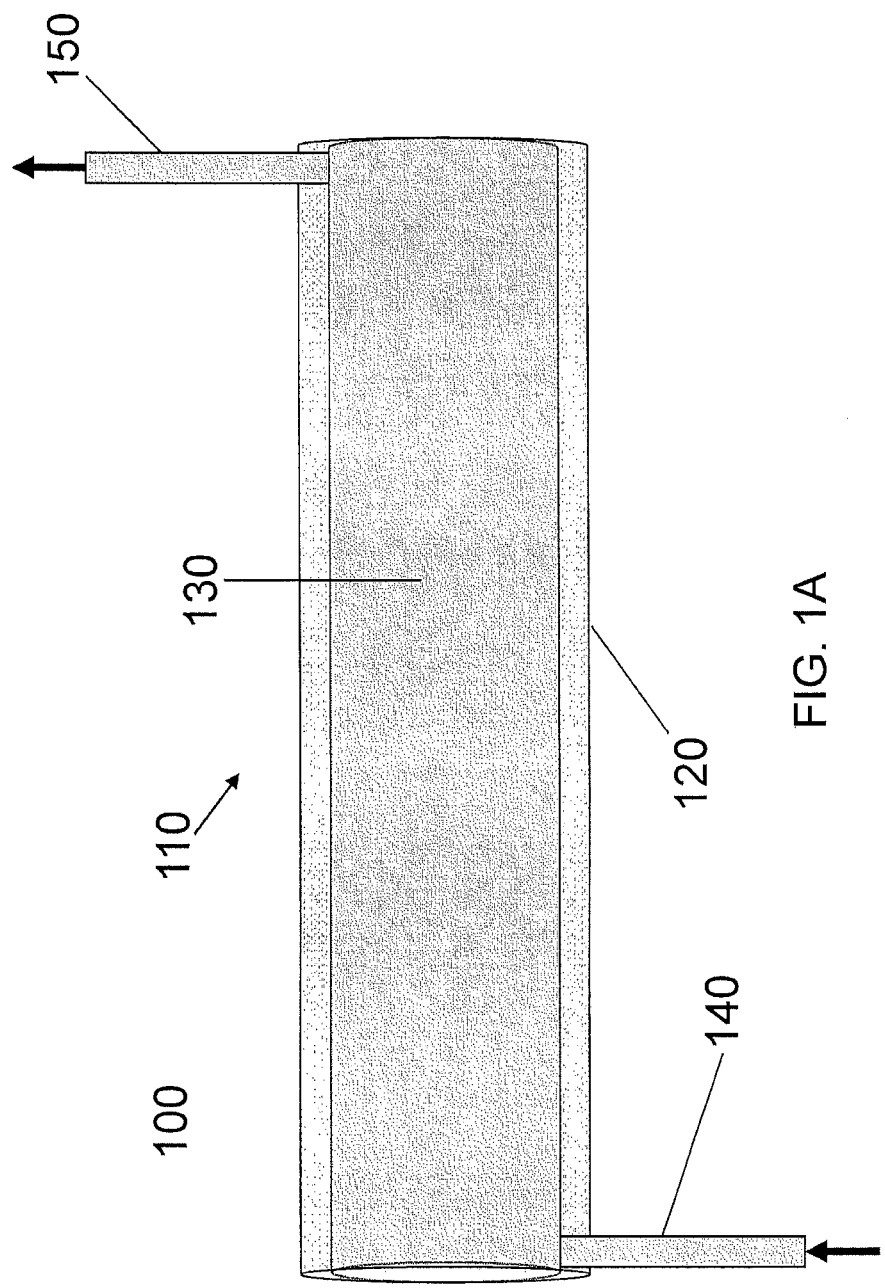
FIG. 1A is a schematic illustration of a perspective view of an apparatus for viral inactivation of liquid media according to this invention that includes one coaxial cylinder.

The invention generally is directed high throughput treatment of a liquid. In a particular aspect, the invention is directed to methods and apparatuses which enable high throughput viral inactivation of liquid media. As used herein, a liquid media includes any liquid or solution in which it is desirable to remove a viral contamination or prevent a potential contamination, including but not limited to buffers, ingestible fluids, injectable solutions, biological fluids, serum, media, bioprocessing solutions, animal-component containing solutions, and therapeutics for human or veterinary use. In one embodiment, a bioprocessing solution is a cell culture media, a conditioned media, a chromatography solution (such as a wash or elution buffer), or a formulation solution. In one embodiment, the liquid media is cell culture media (e.g., serum-containing cell culture media or serum-free cell culture media). In another embodiment, the liquid media is a liquid containing at least one therapeutic protein, such as a monoclonal antibody, a recombinant protein, or an enzyme.

As used herein, "high throughput" treatment of a liquid means treatment at a flow rate in a range of between about 0.5 liters per minute (lpm) and about 50 liters per minute, or between about 0.5 liters per minute and about 5 liters per minute, or between about 5 liters per minute and about 10 liters per minute, or between about 10 liters per minute and about 50 liters per minute. In particular embodiments, a high flow rate is about 1 liter per minute, or 2 liters per minute, or 3 liters per minute, or 4 liters per minute, or 5 liters per minute, or 10 liters per minute, or 20 liters per minute, or 30 liters per minute, or 40 liters per minute, or 50 liters per minute.

Viruses include enveloped viruses, such as, for example, HIV, BIV, Bovine leukemia, Hepatitis C, Hepatitis B, Hepatitis G, Herpesvirus, Cache valley virus, Poxviruse, Influenza virus, Parainfluenza virus, Alphavirus, Bornavirus, Vesicular stomatitis virus, Voronavirus, PRRSV, LDHEV, BVDV, and Flavivirus, and non-enveloped viruses, such as, for example, Hepatitis A, Hepatitis E, Parvovirus, Calicivirus, Vesivirus, Astrovirus, Picornavirus, Enterovirus, Rhinovirus, Kobuvirus, Teschovirus, Circovirus, Adenovirus, Reovirus, and Rotavirus. In one embodiment of the invention the apparatus or method of the invention is used for inactivation of an enveloped virus. In another embodiment of the invention the apparatus or method of the invention is capable of inactivation of a non-enveloped virus. Viral inactivation means the apparatus and methods of this invention are capable of at least a 2 log reduction, preferably at least a 3 log reduction, more preferably at least a 4 log reduction, most preferably at least a 5 log reduction or more, in the concentration of viruses, compared to the concentration of viruses in an untreated control media. One of ordinary skill in the art will appreciate that measuring viral reduction may be based upon common practices in the art, such as providing an untreated control that has been spiked with a measured amount of known virus and comparing the untreated control to the level attained following treatment with the apparatus or methods of the invention. See Wang, J., Mauser, A., Chao, S.-F., Remington, K., Treckmann, R., Kaiser, K., Pifat, D., and Hotta, J., *Virus inactivation and protein recovery in a novel ultraviolet-C reactor*, Vox Sanguinis 86: 230-238 (2004); Chevrefils, G., Ing, B., Caron, E., Wright, H., Sakamoto, G., Payment, P., Benoit, B., and Cairns, W., *UV Dose Required to Achieve Incremental Log Inactivation of Bacteria, Protozoa and Viruses*, IUVA News 8(1): 38-45 (2006).

In one embodiment, shown in FIG. 1A, an apparatus 100 for viral inactivation of a liquid, such as a cell culture media, includes one coaxial cylinder 110 constructed of an outer cylinder 120 (with dimensions of length, inner diameter, and outer diameter) and an inner cylinder 130 coaxial with the outer cylinder. The lengths of the outer cylinder 120 and the inner cylinder 130 can vary according to the use. Without limitation, in certain embodiments, the length of the outer cylinder 120 can be in a range of between about 25 cm and about 100 cm, or between about 35 cm and about 90 cm, or between about 45 cm and about 80 cm, or between about 55 cm and about 70 cm. The apparatus further includes a liquid media inlet 140, at least one emitter of type C ultraviolet radiation 145 (shown in FIG. 1B in the cross section of the coaxial cylinder 110) inside the inner cylinder 130, and a liquid media outlet 150. The inner cylinder 130 has a length substantially equal to the length of the outer cylinder 120 and, as shown in FIG. 1B, an outer diameter 120 adapted to form a gap 160 between the outer diameter of the inner cylinder 130 and the inner diameter of the outer cylinder 120. The gap 160 can be in a range of between about 1 mm and about 5 mm. In particular aspects, the gap is about 1 mm, about 2 mm, about 3 mm, about 4 mm, or about 5 mm. The liquid media flows in a substantially cyclonic flow path, shown in FIG. 1E, along all, or a substantial portion of, the gap 160. The cyclonic flow path can include secondary swirling flow in the plane of a cross section along the gap 160 perpendicular to the axis of the coaxial cylinder 110.

Figure 3:
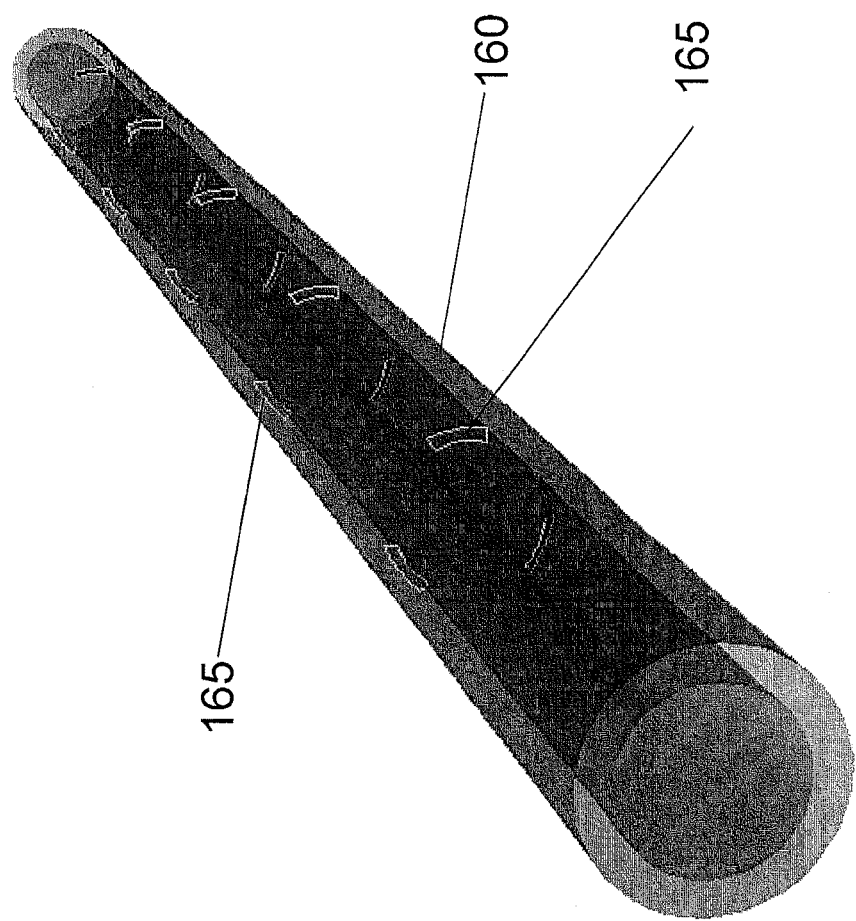
FIG. 3 is a schematic illustration of static mixing elements inside the gap along a coaxial cylinder.

The gap can also optionally include static mixing elements 165 such as baffles or flow deflectors, as shown in FIG. 3. As described herein, the liquid can flow through the gap 160 at a high throughput. Without limitation, in certain embodiments, the flow rate of the liquid media along the gap 160 can be in a range of between about 0.5 lpm and about 50 lpm, or between about 5 lpm and about 40 lpm, or between about 10 lpm and about 30 lpm.

Turning back to FIG. 1A, the liquid media inlet 140 is connected to the outer cylinder 120 preferably at, or proximal to, an end of the outer cylinder 120. The inlet 140 is configured to flow the liquid media in a substantially cyclonic flow path along the gap 160. As shown in FIG. 1B, the inlet 140 is located such that a center line 170 along the inlet 140 intersects a radius 180 of the outer cylinder 120 perpendicular to the center line 170 along the inlet 140 at a location 185 at, or proximal to, the outer diameter of the outer cylinder 120. In one aspect, the inlet 140 is tangential to the outer cylinder 120 and/or the inner cylinder 130, as shown in FIG. 1B.

Figure 1D:
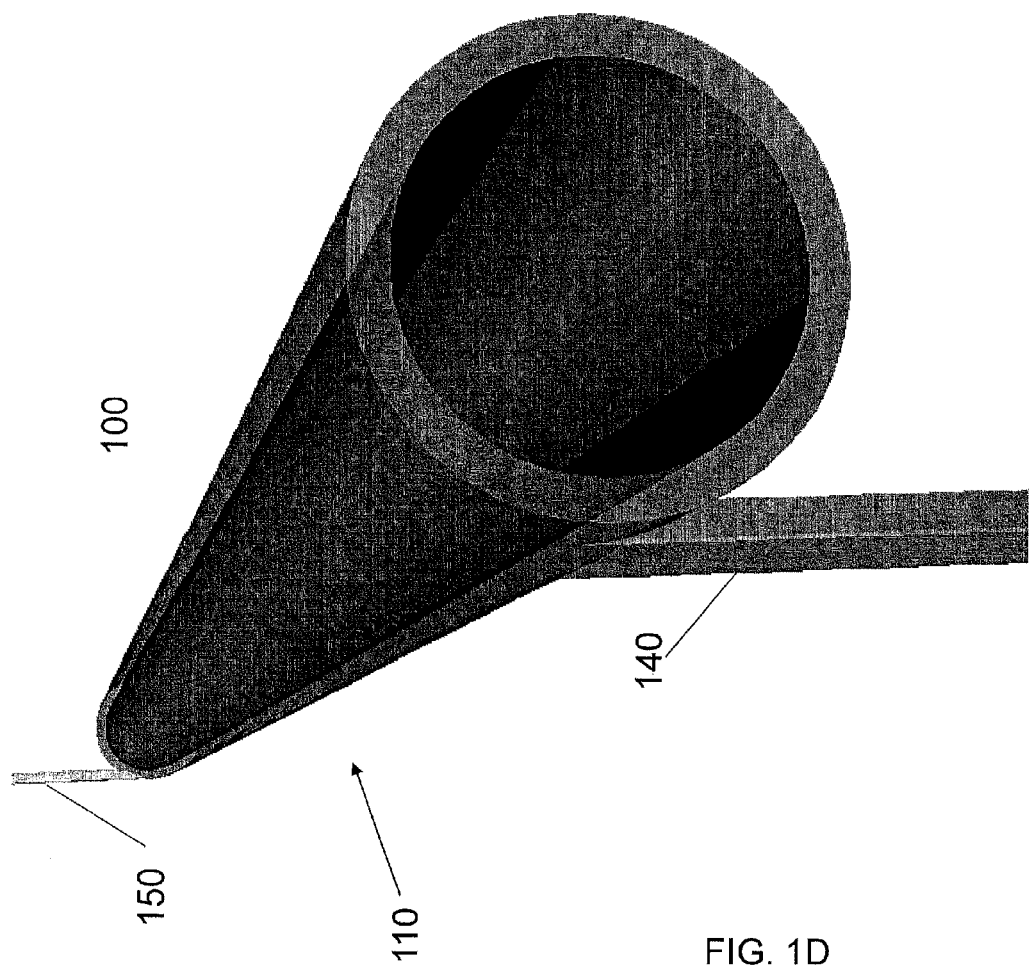
FIG. 1D is a schematic illustration of a perspective view of an apparatus for viral activation of liquid media with a tangential inlet and outlet, both with rectangular cross sections and rounded corners, according to this invention.
Figure 1E:
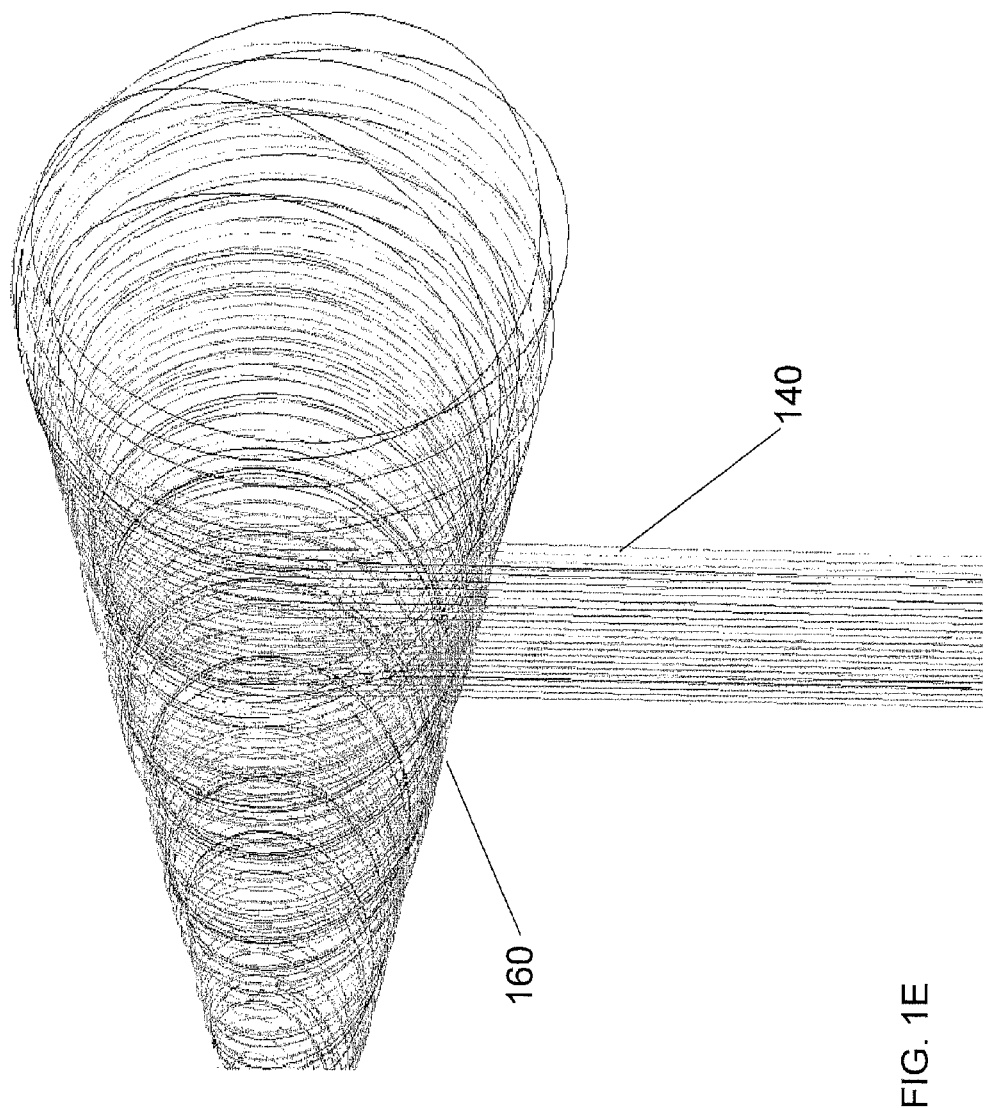
FIG. 1E is a schematic illustration of a cyclonic flow path according to this invention.
Figure 1F:
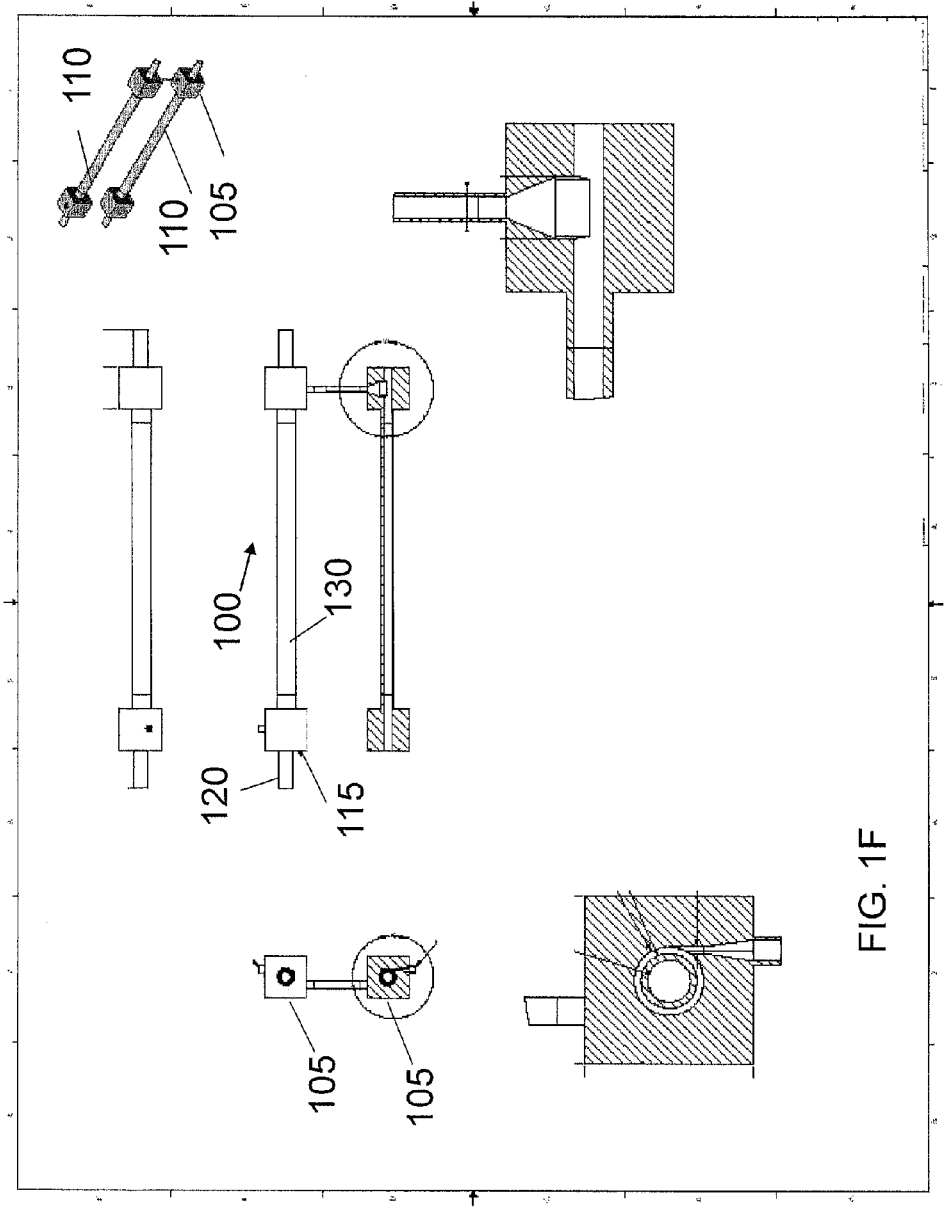
FIG. 1F is a schematic illustration of a specific example of an apparatus for viral inactivation of liquid media according to this invention that includes two coaxial cylinders and a housing around each coaxial cylinder.

The tangential connection of the inlet 140 to the outer cylinder 120 creates or enhances the cyclonic flow along the gap 160. As one of skill in the art will appreciate, other means can be used to enhance or maintain the cyclonic flow along the gap. For example, another feature that enhances the cyclonic flow is minimizing the space, shown in FIG. 1C, between the connection of the inlet 140 and that end of the outer cylinder 120 (i.e., the end of the outer cylinder at which the inlet is located). FIG. 1F is an illustration of a specific example of an apparatus 100 that includes two coaxial cylinders 110 and a housing 105 around each coaxial cylinder 110. The housing 105 includes O-ring seals 115 between the inner cylinder 120 and the outer cylinder 130.

The center line 170 along the inlet 140 forms a radial angle r, shown as 90° in FIG. 1B, with the radius 180 of the outer cylinder 120. The radial angle r can be in a range of between about 90° and about 150°, or between about 100° and about 140°, or between about 110° and about 130°.

As shown in FIG. 1C, a line parallel to the center line 170 along the inlet 140 forms an axial angle a, shown as 90° in FIG. 1C, with the axis 190 of the outer cylinder 120. The axial angle a can be in a range of between about 30° and about 90°, or between about 40° and about 80°, or between about 50° and about 70°.

The inlet 140 can have a variety of shapes, such as a rectangular, square, elliptical, or circular cross section, as shown in the inset in FIG. 1B. An inlet 140 with a rectangular cross section is also shown in FIG. 1D. The inlet 140 with a rectangular or square cross section can also include rounded corners, as shown for a rectangular cross section in FIG. 1D.

Figure 2:
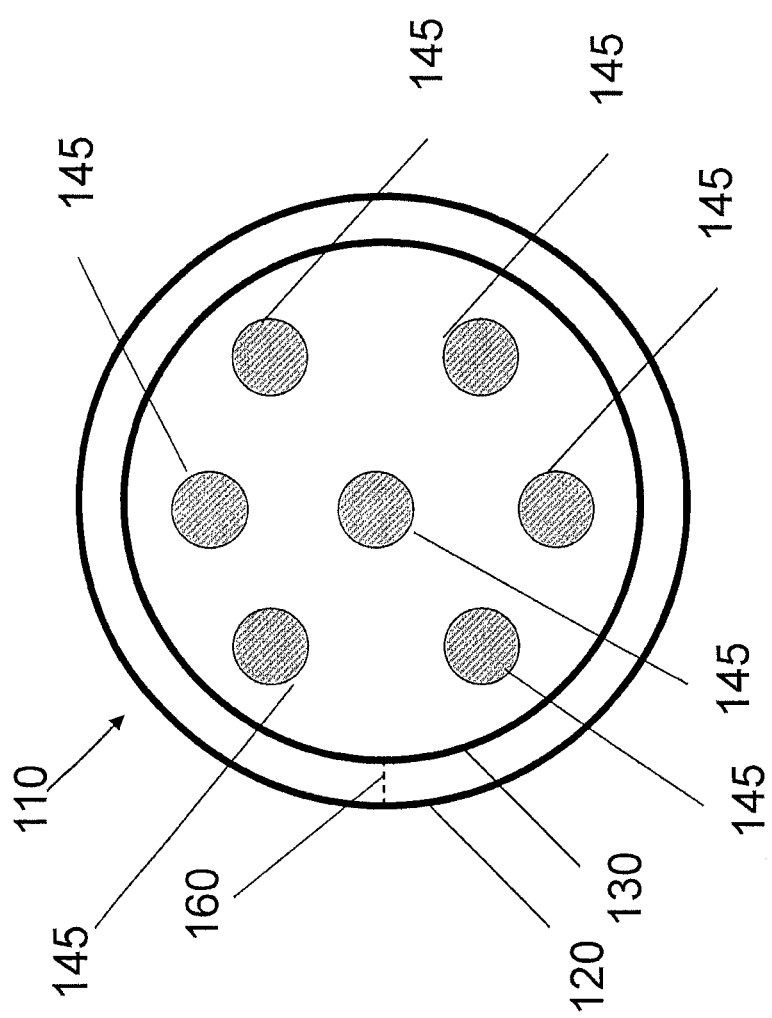
FIG. 2 is a schematic illustration of a cross section of a coaxial cylinder with multiple emitters of type C ultraviolet radiation.

As shown in FIG. 1B, the at least one emitter 145 of type C ultraviolet radiation is placed inside the inner cylinder 130 so as to emit the type C ultraviolet radiation towards the liquid media to be treated with the type C ultraviolet radiation and thereby inactivate viruses in the liquid media, such as a cell culture media. The at least one emitter 145 can have a diameter in a range of between about 1.6 cm and about 2.54 cm. In particular aspects, the at least one emitter 145 can have a diameter of 1.6 cm, 1.7 cm, 1.8 cm, 1.9 cm, 2.0 cm, 2.1 cm, 2.2 cm, 2.3 cm, 2.4 cm, 2.5 cm, and 2.54 cm. Multiple emitters 145 can be placed inside the inner cylinder 130. In particular aspects, from 1 emitter to 8 emitters, such as 2 emitters, 3 emitters, 4 emitters, 5 emitters, 6 emitters, or 7 emitters can be placed inside the inner cylinder 130. As shown in FIG. 2, 7 emitters 145 are evenly distributed inside the inner cylinder 130. The at least one emitter 145 of type C ultraviolet (UVC) radiation can be, for example, a low pressure UVC lamp or a medium pressure UVC lamp, both of which are commercially available. See e.g., UV lamps by Heraeus Noblelight LLC, Duluth, Ga. The at least one emitter 145 emits radiation of a wavelength in a range of between about 200 nm and about 280 nm (the UVC range or type C), or between about 210 nm and about 270 nm, or between about 220 nm and about 260 nm, or between about 220 nm and about 270 nm, or between about 245 nm and about 260 nm. In one aspect, the lamp is monochromatic (within the UVC range) with a wavelength of about 254 nm. The at least one emitter 145 can have a lamp power in a range of between about 80 W and about 200 W. In particular aspects, the at least one emitter 145 can have a lamp power of about 80 W, or about 90 W, or about 100 W, or about 110 W, or about 120 W, or about 130 W, or about 140 W, or about 150 W, or about 160 W, or about 170 W, or about 180 W, or about 190 W, or about 200 W.

Figure 10:
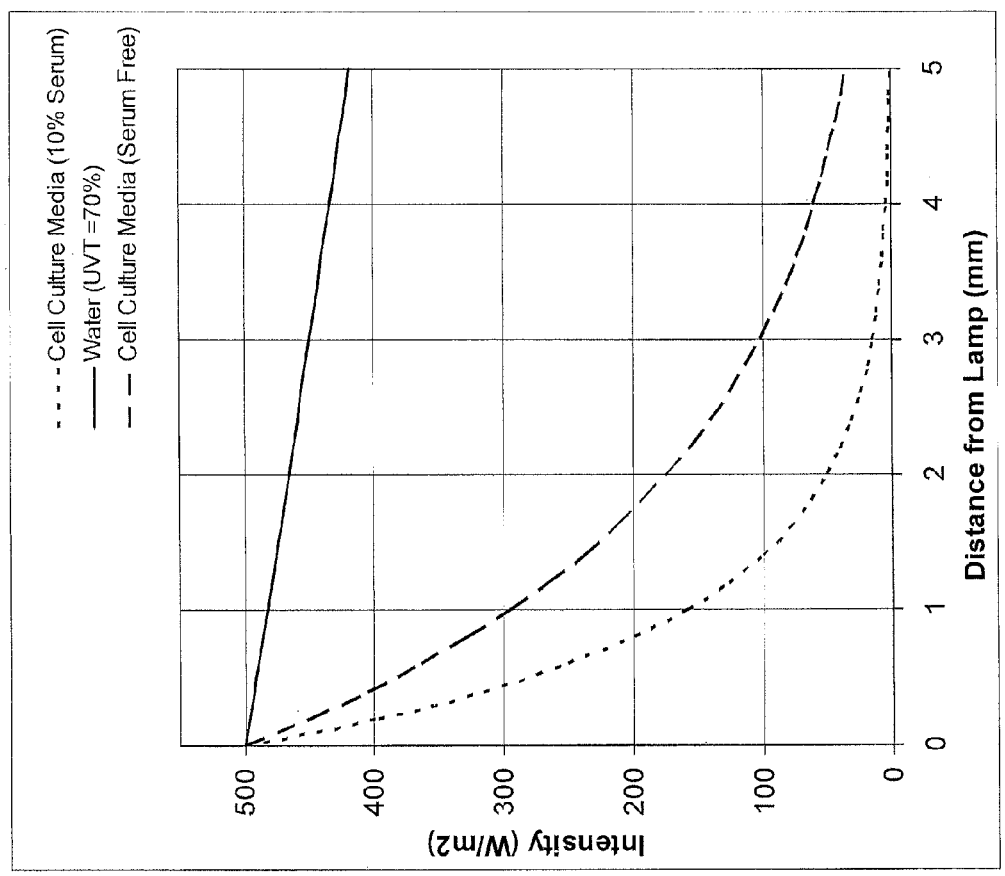
FIG. 10 is a graph of the radiation intensity at 254 nm as a function of radial distance from the quartz sleeve for water, serum-free cell culture media, and serum-containing (10% vol) cell culture media.

As one of ordinary skill in the art will appreciate, penetration of UVC radiation drops exponentially with distance according to the Beer-Lambert law. As shown in FIG. 10, the UVC transmittance of serum-free cell culture media was about 0.1% at 254 nm (UVC absorbance of about 3 absorbance units), while the UVC transmittance of 10 vol % serum-containing media was about 0.001% at 254 nm (UVC absorbance of about 5 absorbance units), as compared to a UVC transmittance of 70% at 254 nm (UVC absorbance of about 0.15 absorbance units) for water. Typical UVC absorbance of serum-free cell culture media can be in a range of between about 1.5 and about 2.5 absorbance units. Typical UVC absorbance of serum-containing cell culture media can be in a range of between about 2.5 and about 5.5 absorbance units, depending on the serum concentration. As used herein, a low transmittance (i.e., high absorbance) liquid is a liquid with a UVC transmittance at about 254 nm in a range of between about 1% and about 1E-38% (UVC absorbance in a range of between about 2 and about 40 absorbance units), such as a transmittance at about 254 nm in a range of between about 1% and about 1E-5% (UVC absorbance in a range of between about 2 and about 7 absorbance units), or a transmittance in a range of between about 1% and about 1E-8% (UVC absorbance in a range of between about 2 and about 10 absorbance units), or a transmittance in a range of between about 1% and about 1E-13% (UVC absorbance in a range of between about 2 and about 15 absorbance units, or a transmittance in a range of between about 1% and about 1E-18% (UVC absorbance in a range of between about 2 and about 20 absorbance units), or a transmittance in a range of between about 1% and about 1E-23% (UVC absorbance in a range of between about 2 and about 25 absorbance units), or a transmittance in a range of between about 1% and about 1E-28% (UVC absorbance in a range of between about 2 and about 30 absorbance units), or a transmittance in a range of between about 1% and about 1E-33% (UVC absorbance in a range of between about 2 and about 35 absorbance units).

Turning back to FIG. 1A, the outlet 150 is connected to the outer cylinder 120 preferably at, or proximal to, an end of the outer cylinder 120 opposite the inlet 140. The outlet 150 can be configured, in a configuration similar to that of inlet 140, to create or maintain the cyclonic flow of the liquid media (such as a cell culture media) upon exit. Such a configuration is particularly useful when the apparatus of the invention includes multiple coaxial cylinders 110, such as shown in FIGS. 4-7.

The outer cylinder 120 and inner cylinder 130 can be made from a variety of materials. In one aspect, the outer cylinder 120 is made of a metal or material suitable for biopharmaceutical processing, such as stainless steel, typically 316L grade. In another aspect, the inner cylinder 130 is made of a material that is substantially transparent to the UVC radiation, such as fluoropolymer and/or quartz. Optionally, the inner cylinder 130 and outer cylinder 120 can be molded in a variety of shapes to facilitate the cyclonic flow of the liquid. For example, the inner cylinder 130 (e.g., made of fluoropolymer) can be molded to maintain or enhance the cyclonic flow of the liquid while increasing radial mixing through secondary turbulent vortices or eddies, by providing a shape along the gap 160, or by providing static mixing elements, rough surfaces, or ridges along the gap 160. An inner cylinder 130 made of fluoropolymer could also be disposable, for ease of maintenance of the apparatus 100. Examples of fluoropolymer materials that meet Class VI specifications, and are therefore suitable for pharmaceutical applications, include, but are not limited to polytetrafluoroethylene (PTFE), fluoroethylene-propylene (FEP), and perfluoralkoxy (PFA). Saint-Gobain Performance Plastics, Akron, Ohio.

In particular aspects, the apparatus comprises two or more coaxial cylinders. In these embodiments, the apparatus comprises a connector between each of the coaxial cylinders. For example, turning to FIG. 4, the apparatus 100 for viral inactivation of liquid, (e.g., cell culture media) includes a connector 195 between a first coaxial cylinder 110 and a second coaxial cylinder 110. The connector 195 can include static mixer elements. The connector 195 can be configured, in a configuration similar to that of inlet 140 described herein, to create or maintain the cyclonic flow of the liquid media upon exit from the first coaxial cylinder 110.

Figure 5A:
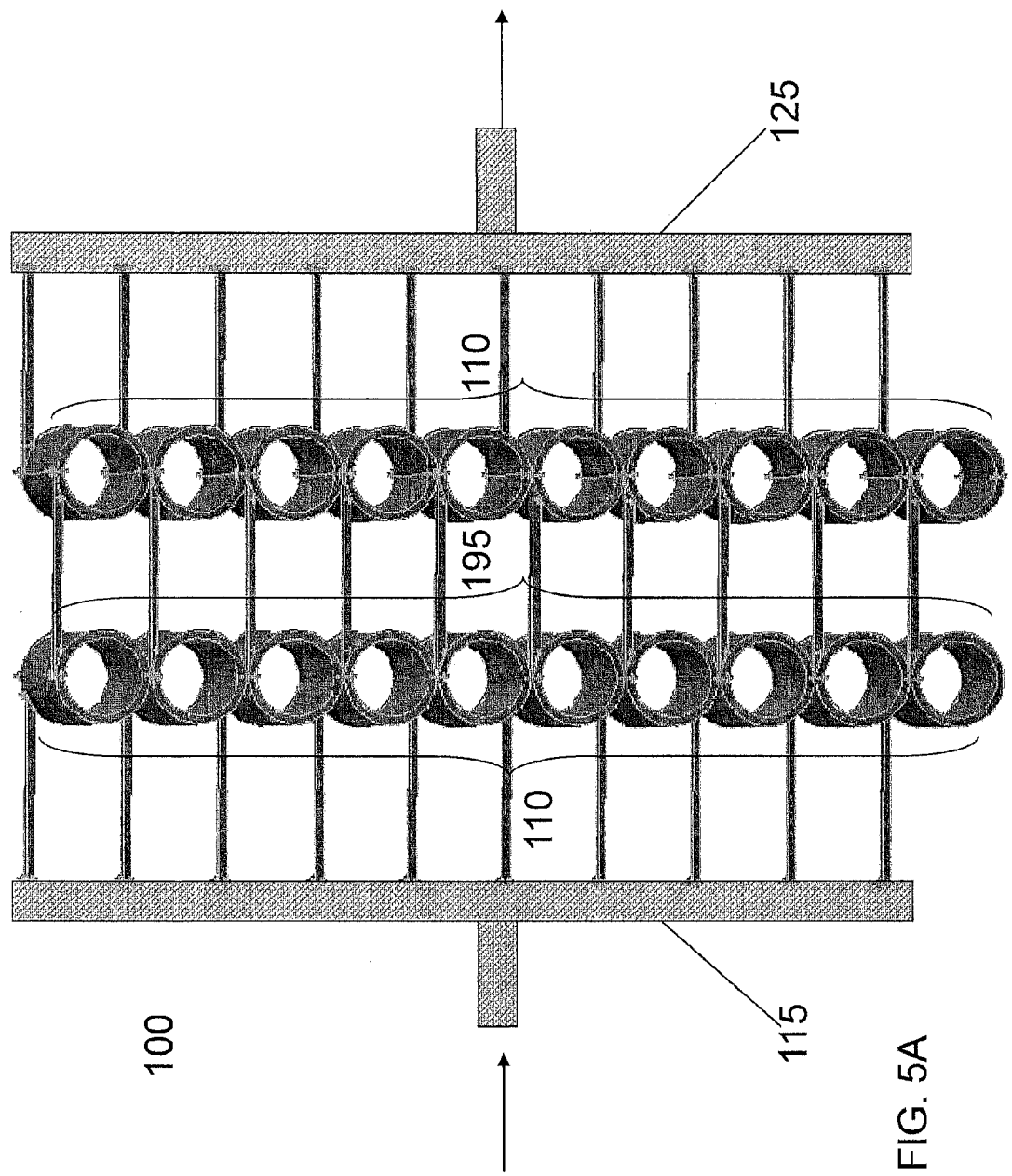
FIG. 5A is a schematic illustration of stacking two rows of coaxial cylinders between an input manifold and an output manifold according to this invention.
Figure 5B:
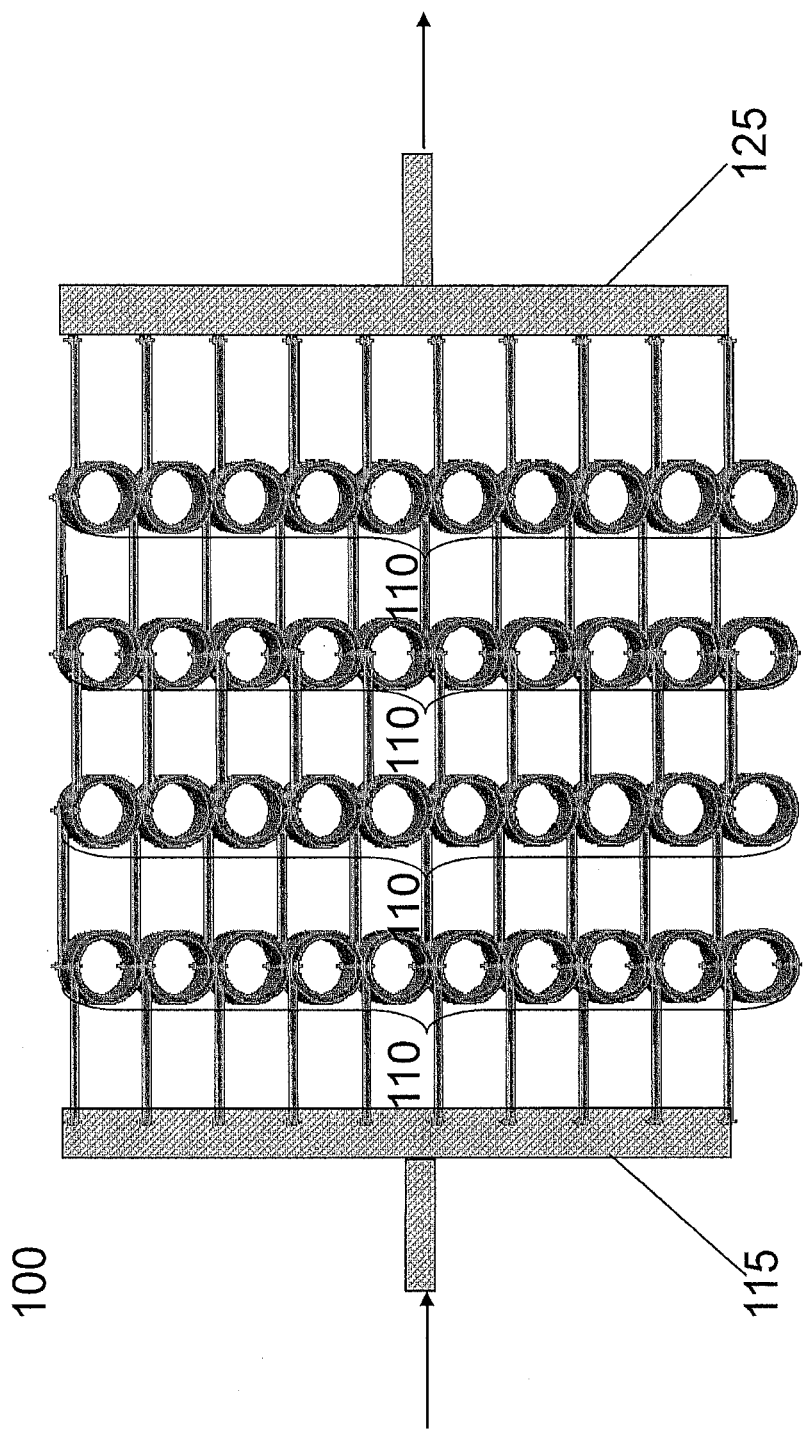
FIG. 5B is a schematic illustration of stacking four rows of coaxial cylinders between an input manifold and an output manifold according to this invention.
Figure 6:
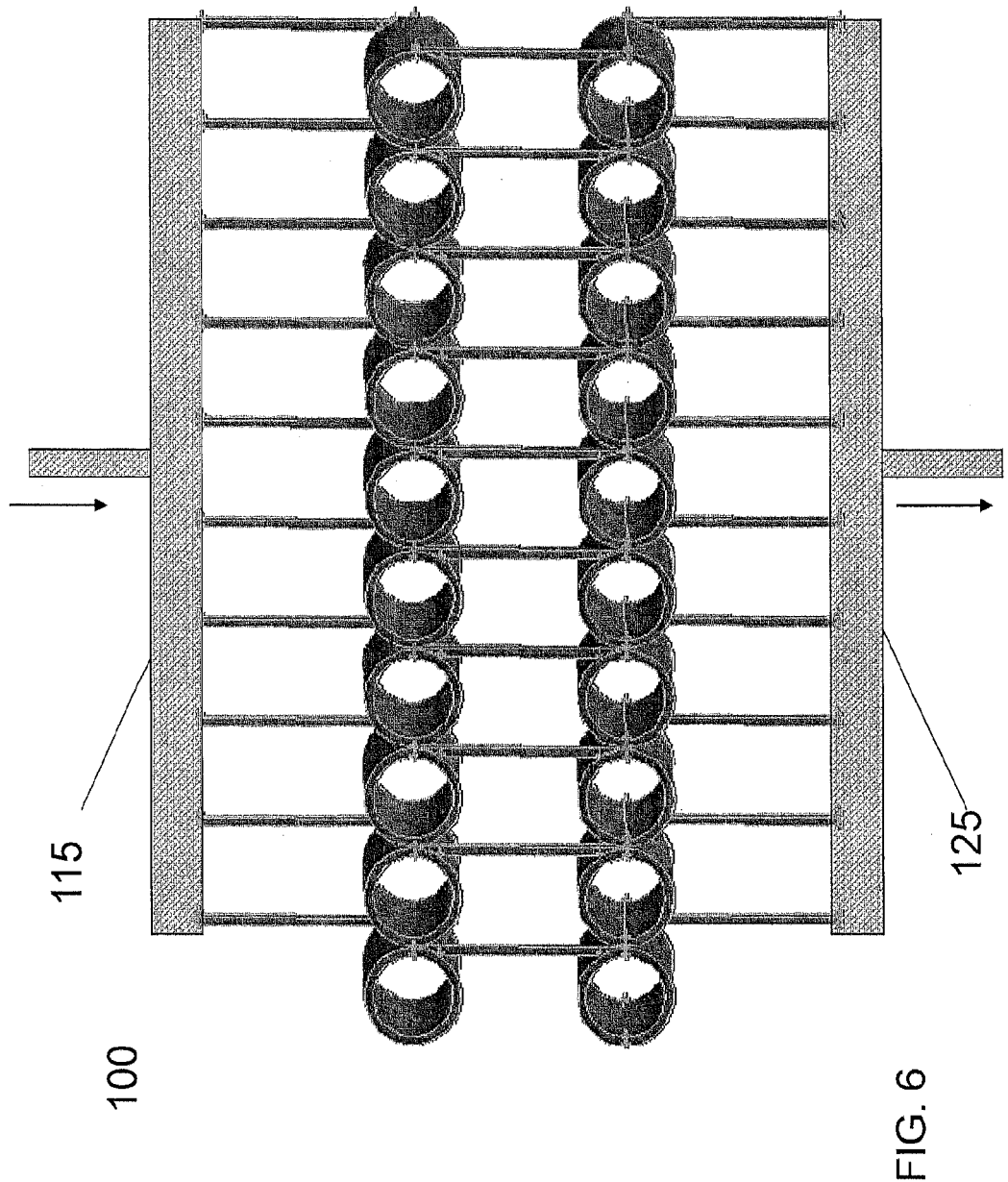
FIG. 6 is a schematic illustration of horizontal stacking two rows of coaxial cylinders between an input manifold and an output manifold according to this invention.
Figure 7A:
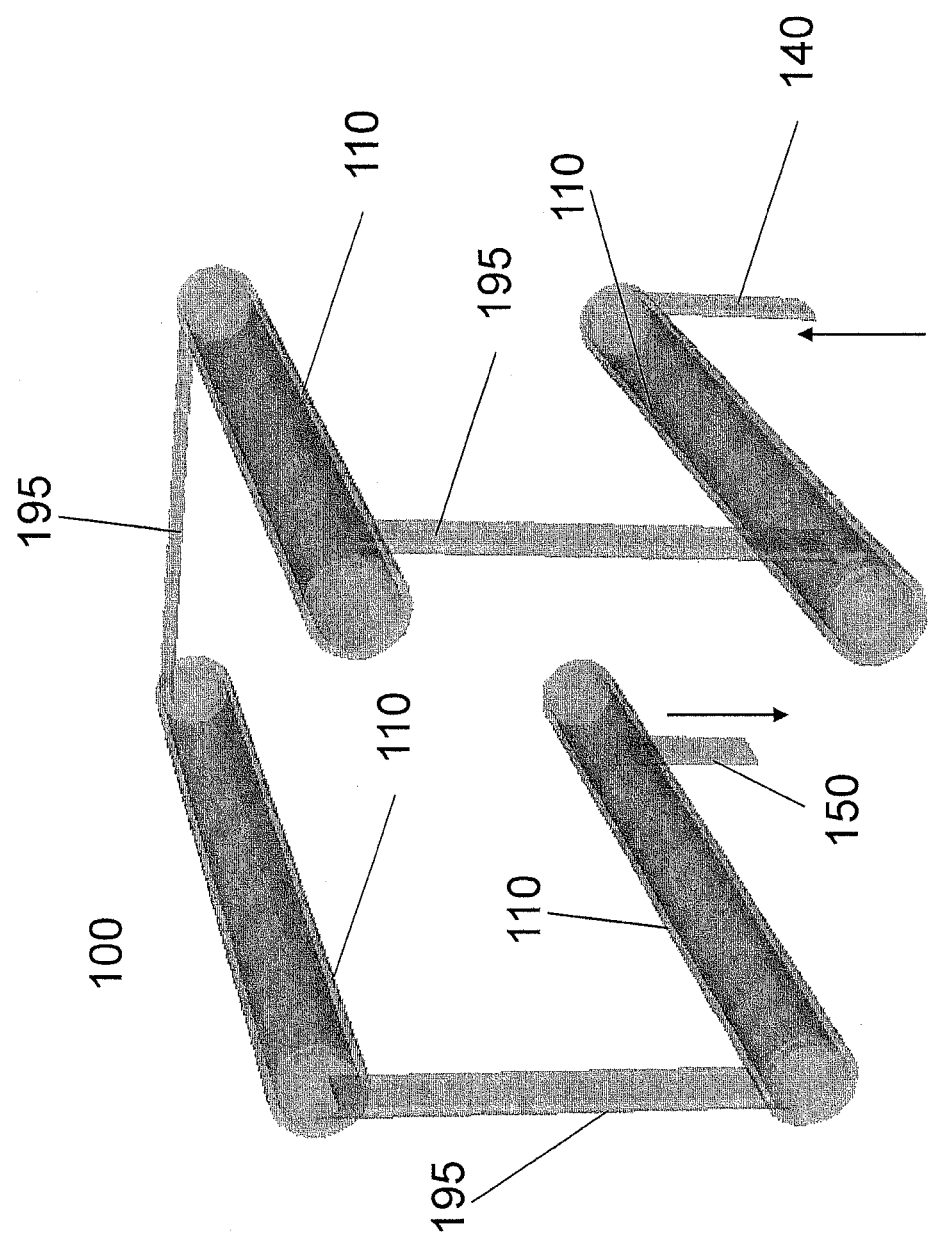
FIG. 7A is a schematic illustration of four coaxial cylinders stacked horizontally and vertically according to this invention.
Figure 7B:
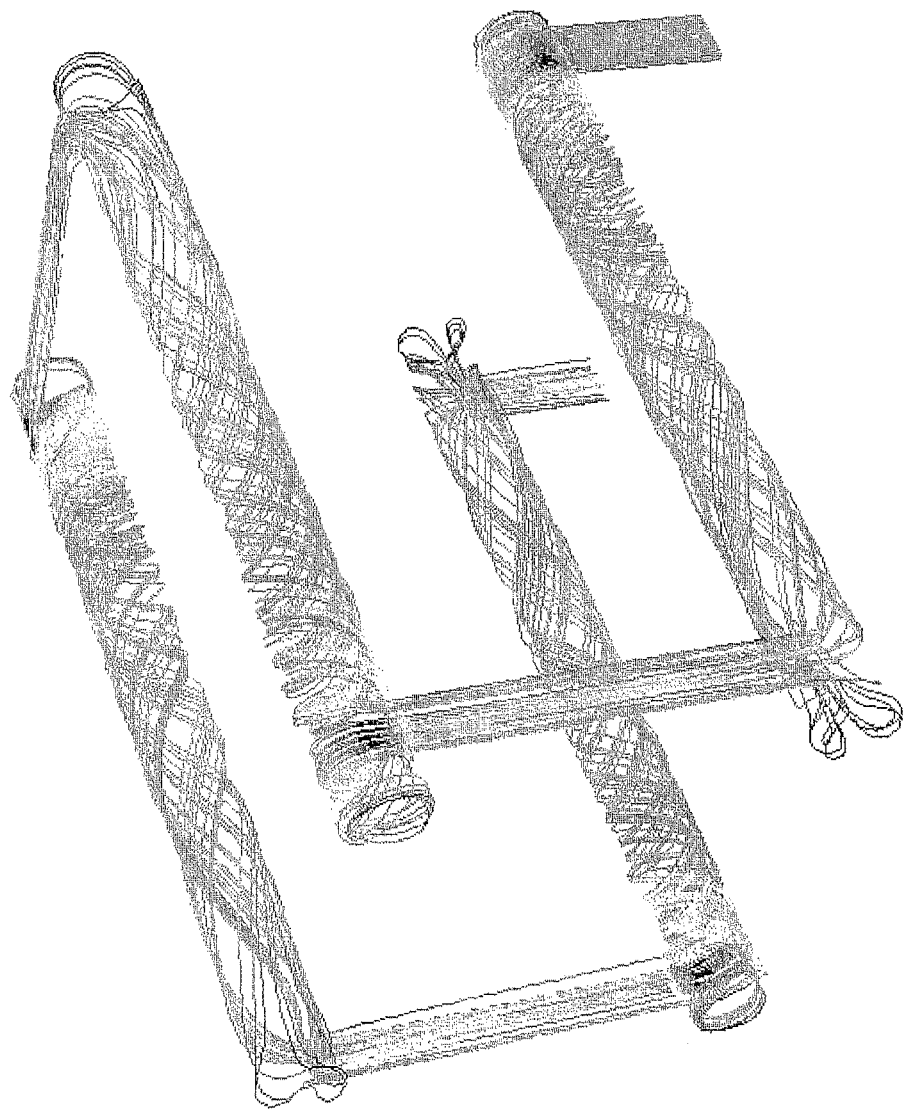
FIG. 7B is a schematic illustration of flow of liquid media through the apparatus shown in FIG. 7A.

As will be appreciated by those of ordinary skill in the art, the apparatus 100 can comprise multiple coaxial cylinders, depending on the particular use (e.g., amount and type of liquid to be treated, etc.). As shown in FIGS. 5A and 5B, such embodiments can further include one or more manifolds. In one aspect, the apparatus 100 comprises at least one inlet manifold 115, and at least one outlet manifold 125 to enable stacking of multiple coaxial cylinders 110. The coaxial cylinders 110 can be stacked vertically, as shown in FIG. 4, or horizontally, as shown in FIG. 6, or as a mixture of vertical and horizontal stacking, as illustrated in FIG. 7A, and the corresponding flow diagram shown in FIG. 7B. One advantage of the apparatus comprising multiple coaxial cylinders is the ability of the apparatus to fit into restricted spaces or into customized space requirements. The stacking arrangements shown in FIGS. 5A, 5B, and 6 can include additional valves (not shown) to shut-off specific coaxial cylinders 110 on a manifold.

In one embodiment, stacking of the coaxial cylinders 110 enable the footprint of the apparatus to be less than or equal to about 5 feet by 5 feet by 5 feet. In another embodiment, stacking of the coaxial cylinders 110 enable the volume of the apparatus to be less than or equal to about 125 cubic feet. In another embodiment, the stacking of coaxial cylinders (either vertically, horizontally, or mixed) enables the apparatus to be fitted around existing manufacturing or other equipment, while still providing a high throughput of liquid media to be treated. Scaling to higher flow rates can involve connecting many units in parallel. For example, in one embodiment, connecting just 10 units in parallel, wherein, in this example, each unit includes 2 coaxial cylinders with 3 mm gaps and operating at 10 lpm, can provide a flow rate 100 lpm for serum-free cell culture media treatment with a pressure drop of 2.5 pounds per square inch (psi), without accounting for additional inlet elbow losses. In one embodiment, the apparatus 100 is rated for a pressure of less than or equal to about 50 psi, in order to enable using the apparatus in process streams that employ pressure downstream of the apparatus, such as for filtration (typically employing up to about 30 psi). In another embodiment, the apparatus 100 is rated for a pressure in a range of between about 25 psi and about 50 psi. With a pressure drop from flow of less than or equal to 5 psi, treatment of serum-containing cell culture media at 100 lpm can be accomplished with 25 coaxial cylinders in parallel, which can fit comfortably in a 5'×5'×5' footprint, and yet have a throughput in a range of between about 2500 liters per hour and about 6000 liters per hour. In particular embodiments, the throughput range can be about 2200 liters per hour, about 2400 liters per hour, about 2500 liters per hour, about 2600 liters per hour, about 2800 liters per hour, about 3000 liters per hour, about 3200 liters per hour, about 3400 liters per hour, about 3600 liters per hour, about 3800 liters per hour, about 4000 liters per hour, about 4200 liters per hour, about 4400 liters per hour, about 4600 liters per hour, about 4800 liters per hour, about 5000 liters per hour, about 5200 liters per hour, about 5400 liters per hour, about 5600 liters per hour, about 5800 liters per hour, or about 6000 liters per hour.

Figure 9:
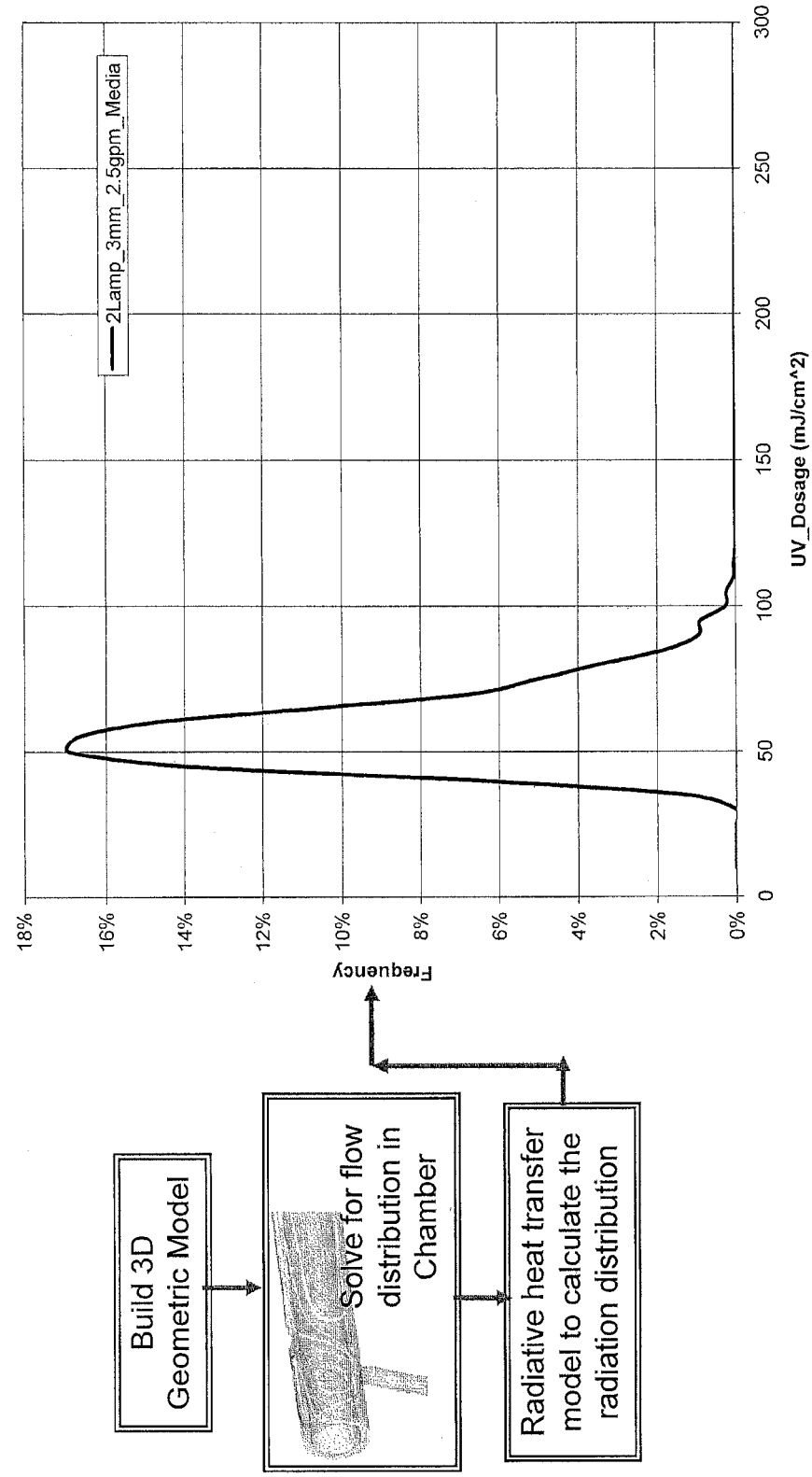
FIG. 9 is a schematic illustration of the workflow for model development.

As will be appreciated by those of ordinary skill in the art, the apparatus can further comprise a variety of optional components. Turning to FIG. 8, in another embodiment, an apparatus 200 for viral inactivation of liquid, (e.g., cell culture media) includes apparatus 100, and, optionally, a pump 210 for pumping the liquid media, (e.g., cell culture media) through the apparatus 100. Alternatively, the head pressure from a liquid holding tank 215 can be used to flow liquid media, (e.g., cell culture media) through the apparatus 100. The apparatus 200 can further optionally include a monitor 220 (marked with a D in FIG. 9) which indicates dosage of radiation to which the liquid media, (e.g., cell culture media) has been exposed, and further optionally include one or more shut-off valves 240.

The dose of radiation can be in a range of between about 5 mJ/cm$^2$ and about 100 mJ/cm$^2$, or between about 10 mJ/cm$^2$ and about 90 mJ/cm$^2$, or between about 20 mJ/cm$^2$ and about 80 mJ/cm$^2$, or between about 30 mJ/cm$^2$ and about 70 mJ/cm$^2$, or between about 40 mJ/cm$^2$ and about 60 mJ/cm$^2$. In one aspect, the minimum dose of radiation to achieve the desired at least 4 log reduction in concentration of non-enveloped virus is about 20 mJ/cm$^2$. In another aspect, the minimum dose of radiation to achieve the desired at least 6 log reduction in concentration of virus is about 30 mJ/cm$^2$. In yet another aspect, the minimum dose of radiation to achieve at least a 15 log reduction (theoretical basis) in concentration of virus is about 50 mJ/cm$^2$. The apparatus 200 can further optionally include a liquid media flow rate control valve 230 (marked with an F in FIG. 9) that can regulate and optionally turn off the liquid media flow if needed, as described below. The media flow rate can be in a range of between about 0.5 liters per minute and about 50 liters per minute. The apparatus 200 can also optionally include a shut-off valve 240 upstream of the apparatus 100 to turn off the flow of media, and a flushing system 250 (marked with a W in FIG. 9) to flush out liquid media (e.g., cell culture media) that has been over-exposed or under-exposed to radiation. When the flushing system 250 is operating, the flow control valve 230 is closed, and the media is sent to disposal or another holding tank through the shutoff valve 240 downstream of apparatus 100. One of skill in the art will appreciate that the optional elements of apparatus 200 can be configured in a variety of ways.

Depending on the liquid to be treated, a person of ordinary skill in the art will appreciate that the gap dimension, length of the coaxial cylinder, and flow rate of the liquid can be adjusted to get the desired viral inactivation treatment. In a specific embodiment, with a 3 mm gap and an inlet and a connector tangential to the outer cylinder, and two coaxial cylinders in series, serum-free or serum-containing cell culture media can be exposed to a minimum dosage of radiation in a range of between about 20 and about 30 mJ/cm$^2$, with about 90% of cell culture media being exposed to a dosage of radiation of less than about 80 to about 100 mJ/cm$^2$, with an average dosage of radiation in a range of between about 50 and about 60 mJ/cm$^2$, for a flow rate in a range of between about 3 and about 5 liters per minute, and for a cell culture media having an ultraviolet absorbance in a range of between about 2 and about 5 absorbance units, with 1 to 2 coaxial cylinders including 1 lamp per cylinder.

The apparatus can be used for a variety of purposes, such as for any liquid treatment at high throughput, e.g., in the water or food industries (treatment of beverages, for example). In one embodiment, cell culture media can be treated with the methods and apparatus of the invention.

Cell culture media, as well as supplements thereto, are well known in the art. A large variety of cell culture media are commercially available from a variety of suppliers, such as, e.g., Life Technologies, Inc. (Carlsbad, Calif.), Sigma-Aldrich (St. Louis, Mo.), Thermo Fisher Scientific (Waltham, Mass.), Becton Dickinson & Co. (Franklin Lakes, N.J.). Cell culture media are available for cultures of prokaryotic cells, eukaryotic cells, and archeal cells. For example, cell culture media is available for bacteria, insect cells, archeal cells, plant cells, yeast, mammalian cells, stem cells, neuronal cells and other cell types. Cell culture media may comprise components which are each chemically defined (such as in a chemically-defined medium) or may include one or more components which are less defined, such as extracts from plant, animal or mineral sources. As is well known in the art, cell culture medium may be supplemented with one or more nutrients, such sugars, salts, vitamins, buffers, extracts, chemicals, or other nutrients which assist in the cell growth, production or stabilization of the culture. As is also well known in the art, cell culture medium may be supplemented with serum. For example, animal serum is well known for use in cell culture. For example, commonly used animal sera for mammalian cell culture includes but is not limited to Donor Bovine Serum (DBS), Fetal Bovine Serum (FBS), or Calf Serum.

In certain embodiments, the methods and apparatuses of the invention are designed to deliver UVC doses to a cell culture medium (with or without supplementation) which dose is capable of killing virus. In certain embodiments, the methods and apparatuses of the invention are designed to deliver UVC doses to a cell culture medium (with or without supplementation) which dose is capable of mitigating the risk of the presences of an infectious agent, such as a virus.

In a particular aspect, a method of inactivating viruses in cell culture media includes introducing cell culture media into at least one coaxial cylinder that includes a gap along the length of the cylinder between the outer diameter of an inner cylinder and the inner diameter of an outer cylinder. In another embodiment, the apparatus includes multiple coaxial cylinders. In yet another embodiment, the apparatus includes a manifold of coaxial cylinders. The media is introduced through an inlet configured to flow the cell culture media along a substantially cyclonic flow path along the gap. The method further includes irradiating the cell culture media with at least one emitter of type C ultraviolet radiation placed inside the inner cylinder so as to emit the type C ultraviolet radiation towards the cell culture media to thereby inactivate viruses in the cell culture media. The method then includes flowing the cell culture media through a cell culture media outlet connected to the outer cylinder at, or proximal to, an end of the outer cylinder opposite the inlet. In one embodiment, the cell culture media contains serum, in a range of between about 2 vol % and about 12 vol %. In particular aspects, the cell culture media contains 4 vol % serum, 6 vol % serum, 8 vol % serum, or 10 vol % serum. In another embodiment, the cell culture media is serum-free. In yet other embodiments, the cell culture media is animal-derived-component-free (ADC-free), or chemically defined. In another embodiment, the cell culture media is cell culture media intended for fed-batch.

In another aspect, the method of inactivating viruses can be applied downstream in a biopharmaceutical process to liquid media that comprises at least one therapeutic protein, such as a monoclonal antibody, an enzyme, a fusion protein, or a recombinant protein. In certain embodiments, the liquid media is a chromatography liquid, such as a solution containing a wash, elution or resin. In other embodiments, the liquid media is a formulated or reconstituted solution of a therapeutic protein.

EXAMPLE 1

Apparatus with 5 mm Gap

The design of the apparatus 100 shown in FIG. 4 employs computer simulation based on first principles of fluid dynamics and radiation modeling. The workflow of model development is shown in FIG. 9. First, a detailed 3D geometric model of the apparatus was constructed. The apparatus 100 consists of two UV treatment chambers 110 which contains the UV lamp (tube lamp) in its core surrounded by a quartz tube that separates the lamp from the fluid side. The liquid media is flowed along the gap between the quartz tube and the outer cylinder wall.

Computational fluid dynamics (CFD) was used as a tool in solving for the flow distribution in this model of an apparatus for viral inactivation of liquid media. Fluent, Inc., (Lebanon, N.H.). CFD involves solving first-principles-based flow equations numerically at each control volume (the reactor geometry is discretized into millions of control volumes) using the finite volume method. S. V. Patankar, *Numerical Heat Transfer and Fluid Flow,* Hemisphere, Washington, D.C., 1980.

The flow solution provided information on predicted flow patterns and allowed for visualization of predicted velocities, pressure drop, and turbulence quantities. Subsequent to the flow-solution, a radiation model called the discrete ordinates (DO) model was used to predict the radiation distribution in the computer modeled apparatus. At each control volume in the computer model, the DO model accounted for the incident radiation and took into account absorption, in-scattering and out-scattering based on the absorbance of the potential fluid to be treated, to calculate the resulting radiation leaving this fluid element or control volume. Just like the flow-solution, this computer analysis was conducted on each of the control volumes throughout the computer modeled apparatus, thus providing a distribution of the predicted UV irradiation in the apparatus. For boundary conditions of the radiation model, the wall surfaces were assumed to be “diffuse,” reflecting radiation in all directions.

The incident radiation was calculated based on the UV lamp wattage and efficiency and the surface area of the lamp. Typical lamp efficiencies are in a range of between about 30% and about 40%. Furthermore, a 10% radiation loss was assumed from the lamp surface to the quartz outer surface, and thus the incident intensity (Io) was calculated and assumed to be uniformly distributed across the entire length of the quartz tube in all the following calculations.

As a final step, virtual tracer particles (simulating virus particles, protein particles, fluid packets) were released from the inlet surface. As many as 4000 particles were tracked through the coaxial cylinder 110 based on hydrodynamic forces exerted on them by the fluid. The particles were small enough (assumed size of 1 μm) that they traveled with the flow and provided a good indicator of mixing and exposure to UV dosage along the way.

For each particle, the UV dose was recorded cumulatively as it continued its journey through the coaxial cylinder 110 to the outlet 150 of the apparatus 100. The UV dose was calculated as:

$$\text{UVC Dose (J/m}^2\text{)}=\text{Incident Radiation (W/m}^2\text{)}*\text{Exposure Time (sec)} \quad (1)$$

The result of Eq. 1 was a UVC dose distribution based on the number of particles tracked, which was used as a statistic measure to determine the average dosage, variance, and the minimum dosage for a specified flow-rate, absorbance of media, and geometric design of the coaxial cylinder 110.

All the computer simulations were performed using commercial CFD software—ANSYS FLUENT™ version 6.3.26 on a HP xw8600-Intel Xeon x5450 workstation running Windows XP x64. The analysis used established modeling practices such as high resolution finite volume mesh (more than $1\times10^6$ control volumes), second order numerical discretization for increased accuracy, and achieving deep convergence ($1\times10^{-4}$) of the residuals.

In Examples 2 and 3, predicted results from computer modeling of Example 1 are described. As will be appreciated by those of skill in the art, Lagrangian actinometry is a method of using fluorescent microspheres to confirm the UV dose distributions predicted by computer modeling. Anderson, W. A., Zhang, L., Andrews, S. A., Bolton, J. R. *A technique for direct measurement of UV fluence distribution*, Proceedings of the Water Quality Technology Conference; American Water Works Association: Philadelphia, Pa., 2003. In this approach, fluorescent particles are released upstream from the apparatus, and the particles undergo a chemical reaction when irradiated with UV light. At the outflow of the apparatus, these particles are analyzed with flow cytometry for their degree of fluorescence, which corresponds to the UV dose exposure distribution, thus providing confirmation to the mathematical models described herein.

EXAMPLE 2

5 mm Gap with Tangential Inlet and Connector

Figure 11:
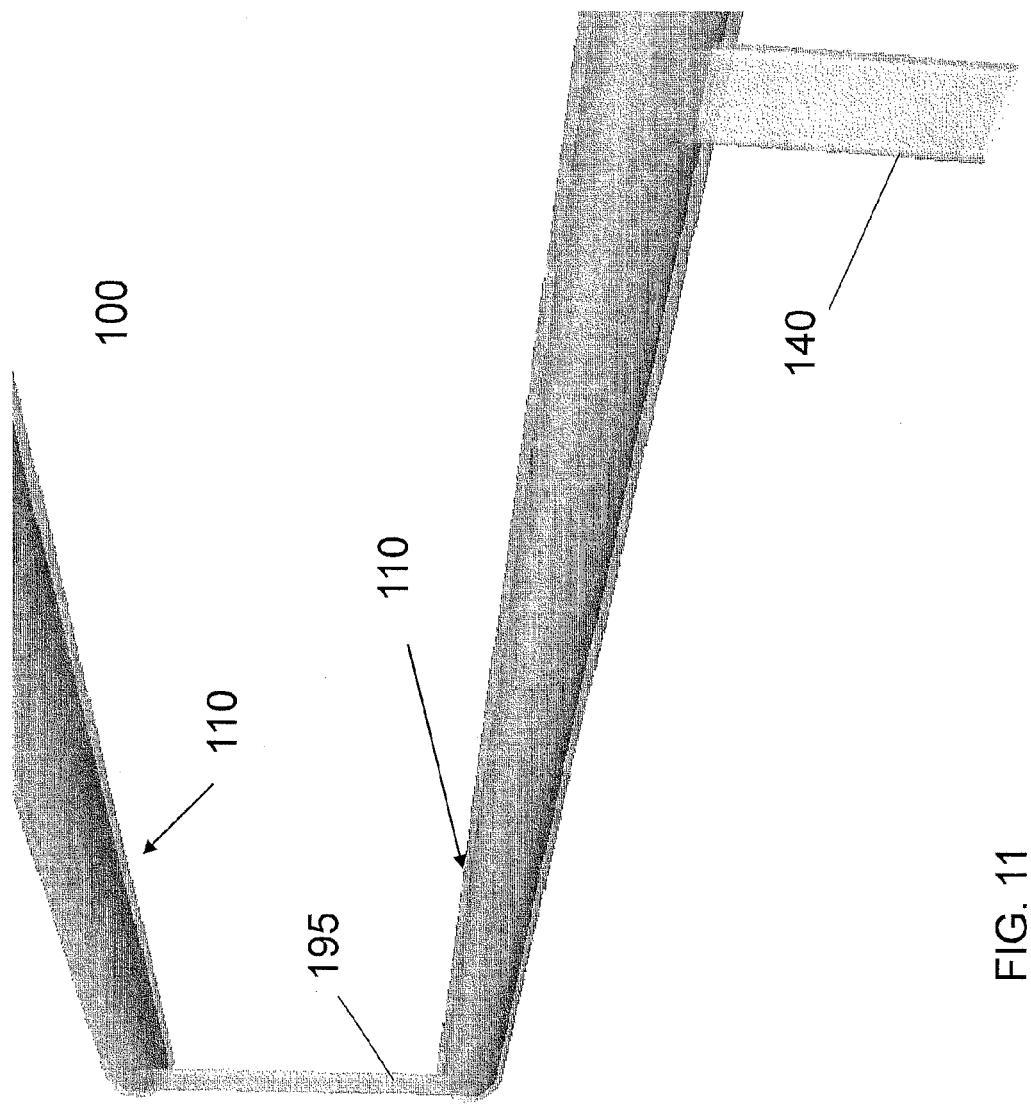
FIG. 11 is a schematic illustration of the apparatus described in Example 2.
Figure 12:
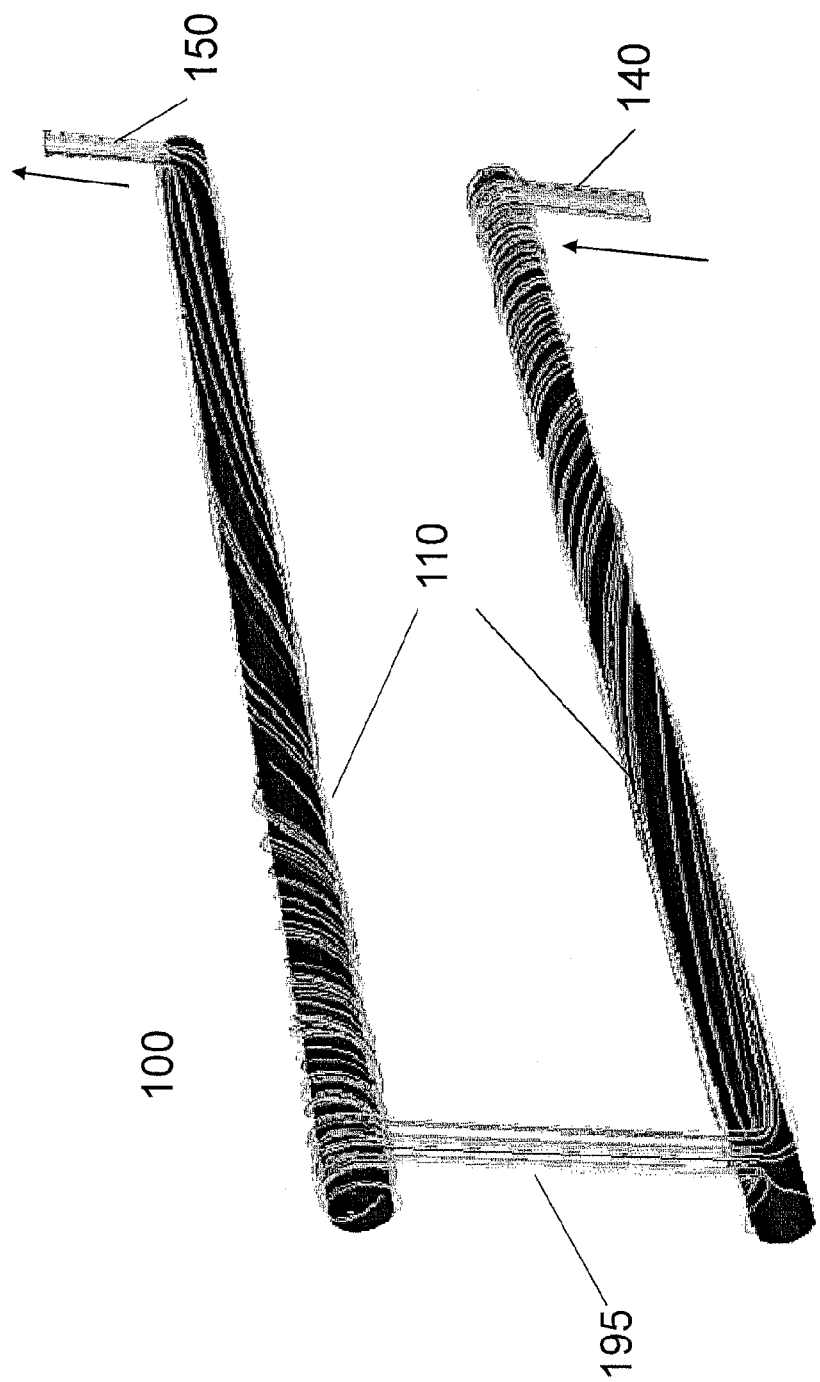
FIG. 12 is a schematic illustration of cyclonic flow paths in the apparatus described in Example 2.
Figure 13:
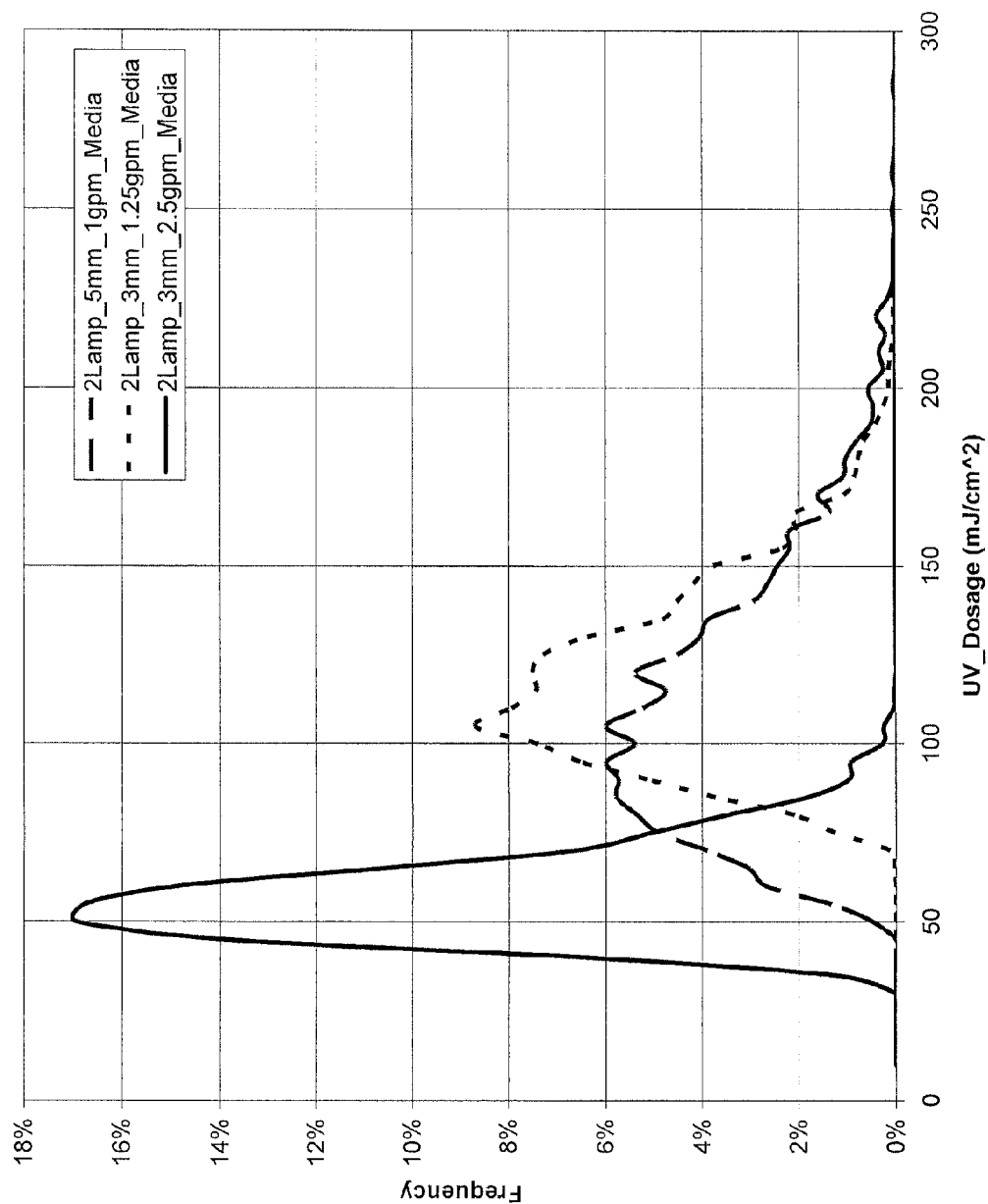
FIG. 13 is a graph of frequency (% of cell culture media exposed) as a function of UV dosage for serum-free cell culture media in the apparatus described in Example 2 (5 mm gap, 3.8 lpm (1 gpm)) and Example 3 (3 mm gap, 4.75 lpm (1.25 gpm) and 9.5 lpm (2.5 gpm)).
Figure 14:
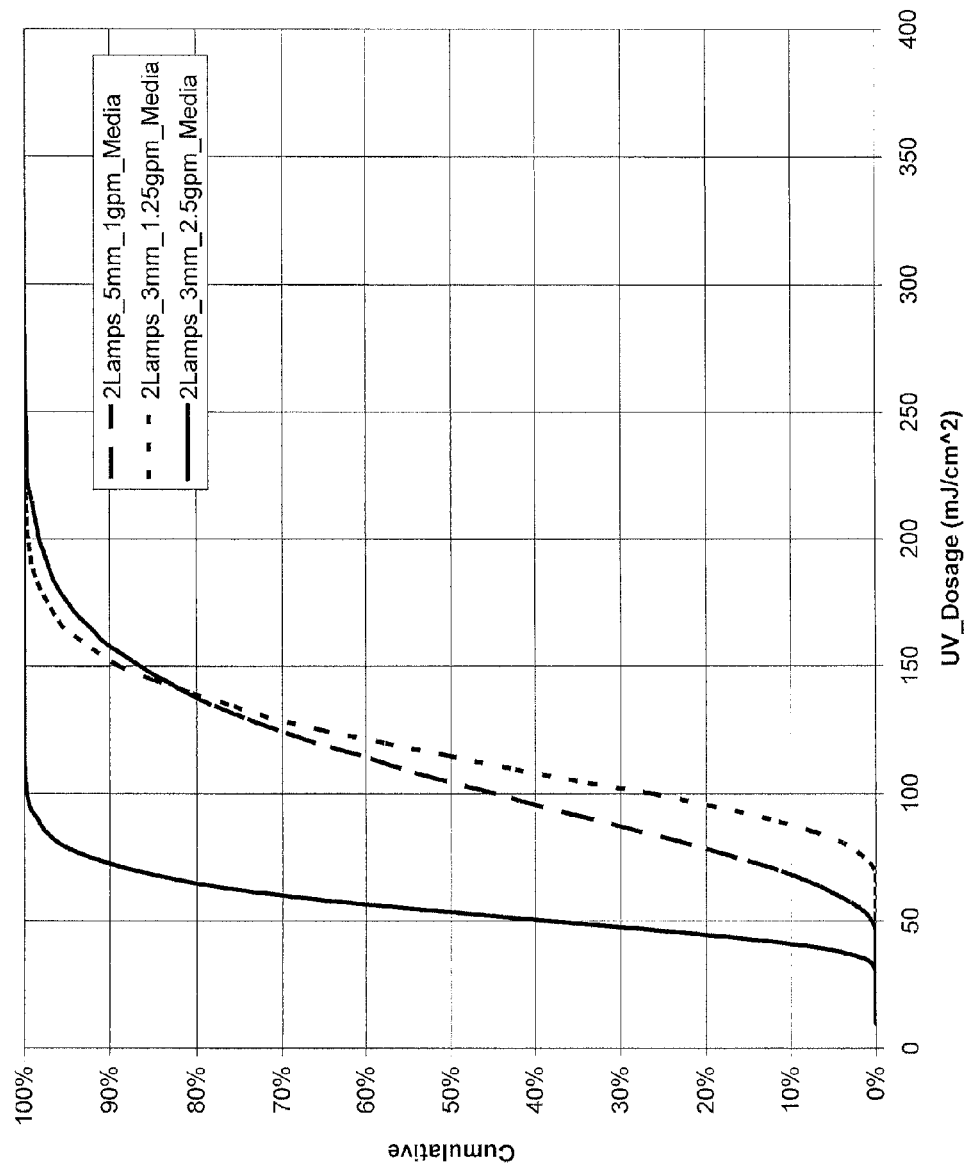
FIG. 14 is a graph of % particles (cumulative dosage) as a function of UV dosage for serum-free cell culture media in the apparatus described in Example 2 (5 mm gap, 3.8 lpm (1 gpm)) and Example 3 (3 mm gap, 4.75 lpm (1.25 gpm) and 9.5 lpm (2.5 gpm)).

A design iteration, shown in FIG. 11, employs a gap of 5 mm, a tangential inlet 140, and a tangential connector 195 to eliminate dead spots and enhance mixing. Tangential inlets and connectors create a cyclonic flow path that results in better mixing, thus potentially narrowing the UV dose distribution. The predicted flow distribution, shown in FIG. 12, shows the cyclonic flow path, although, given the length of the tube, the initially tight swirl in the flow eventually tries to straighten out. The predicted UV dose distribution of this design, labeled as "5 mm," is shown in FIG. 13. The predicted cumulative distributions results, shown in FIG. 14, provide a direct indicator of variance, since the change in slope of the cumulative distribution is a direct indicator of variance. The variance for this design is around 31.7%.

EXAMPLE 3

3 mm Gap with Tangential Inlet and Connector

This design involves a fluid gap 160 of 3 mm instead of 5 mm in addition to the tangential inlet 140 and tangential connector 195. The predicted results from this design are shown in FIGS. 13 and 14, labeled as "3 mm." The predicted variance for serum-free media shows a predicted substantial reduction to 21.26% which provides a very narrow UV dose distribution. The predicted cumulative distribution with a steep slope, shown in FIG. 14, predicts a strong indicator of the design improvement feature. For example, for a flow-rate of 2.5 gallons per minute (2.5 gpm or 9.5 lpm) of serum-free cell culture media, the average dose is 57.8 mJ/cm$^2$ (milli Joules per square centimeter) with a minimum dosage of 30 mJ/cm$^2$. As shown in FIG. 14, 90% of the serum-free cell culture media will be exposed to a maximum dosage of 75 mJ/cm$^2$, and 100% of serum-free cell culture media will be exposed to a dose of less than 100 mJ/cm$^2$.

Figure 15:
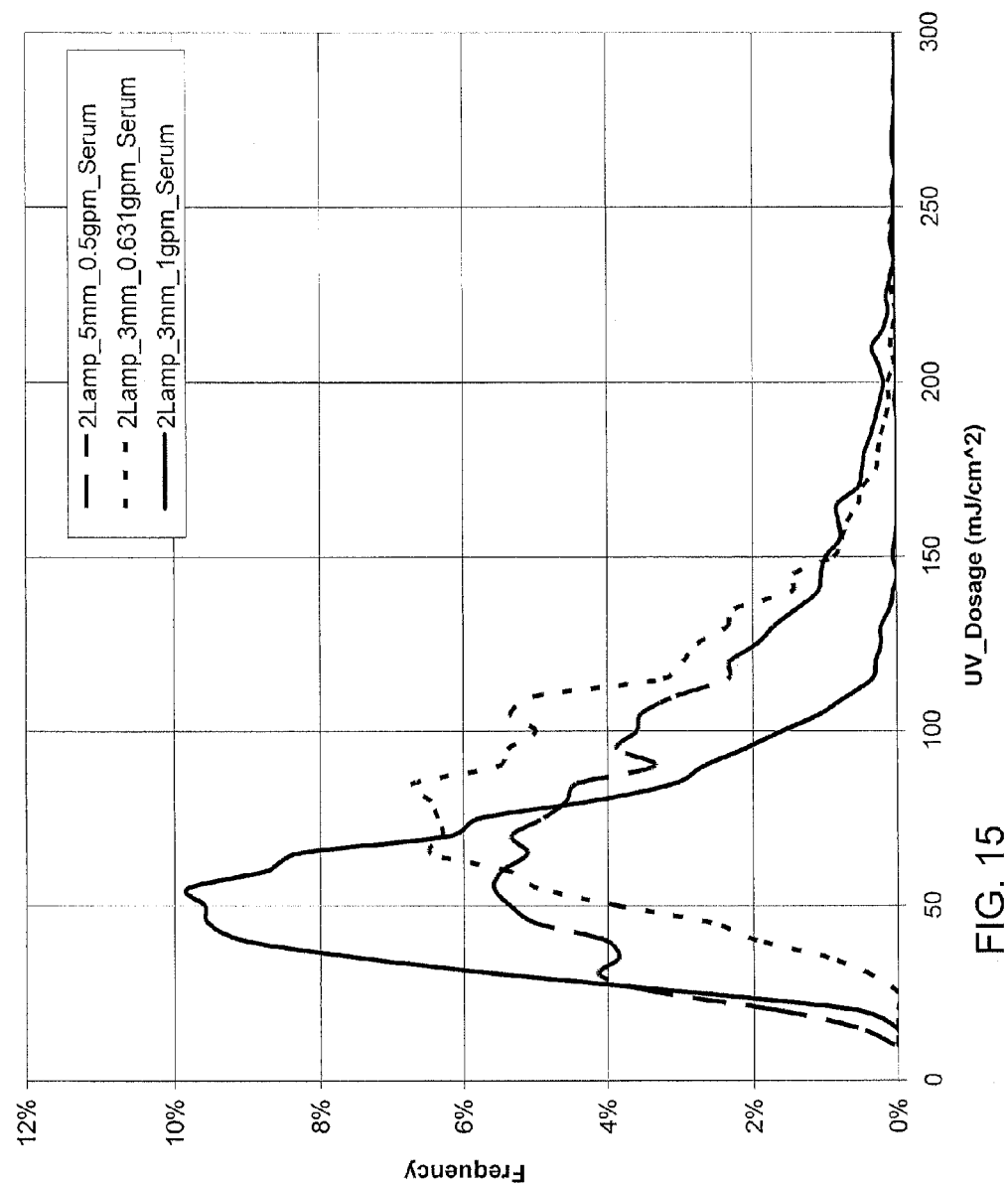
FIG. 15 is a graph of frequency (% of cell culture media exposed) as a function of UV dosage for serum-containing cell culture media in the apparatus described in Example 2 (5 mm gap, 1.9 lpm (0.5 gpm)) and Example 3 (3 mm gap, 2.4 lpm (0.631 gpm) and 3.8 lpm (1 gpm)).
Figure 16:
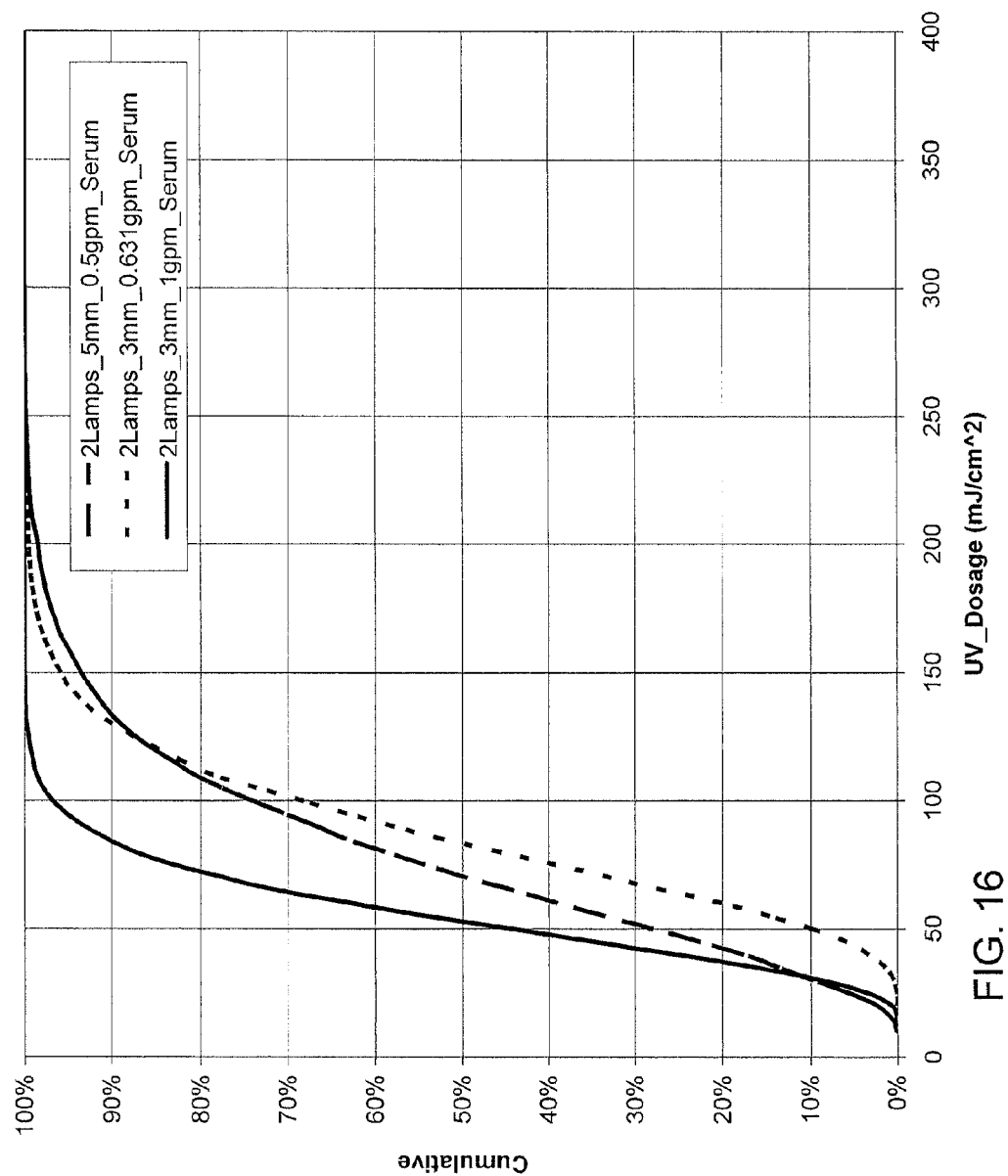
FIG. 16 is a graph of % particles (cumulative dosage) as a function of UV dosage for serum-containing cell culture media in the apparatus described in Example 2 (5 mm gap, 1.9 lpm (0.5 gpm)) and Example 3 (3 mm gap, 2.4 lpm (0.631 gpm) and 3.8 lpm (1 gpm)).

For serum-containing (10 vol %) cell culture media, shown in FIGS. 15 and 16, predictions are similar, with a narrower UV dose distribution. In particular, for serum-containing cell culture media, the distribution predicts long tailing while the minimum dosage remains typically below 20 mJ/cm$^2$. With the design for a 3 mm fluid gap and tangential inlets, the dosage distribution is predicted to be substantially narrowed with the minimum dosage at 30 mJ/cm$^2$ and, as shown in FIG. 16, 90% of serum-containing cell culture media getting an exposure of less than 85 mJ/cm$^2$ for a flow rate of 1 gpm (3.8 lpm), with an average dosage of 58 mJ/cm$^2$.

It is predicted that the apparatus with a liquid gap of 3 mm and tangential inlet and connectors, will provide a sufficiently narrow UVC dose distribution for both serum-free cell culture media and serum-containing cell culture media. The pressure drop within this unit with a parallel configuration is predicted to be well within the limit of 5 psi even for high flow rates. The predicted pressure drop at the higher flow rate of 100 lpm is 2.5 psi, while the predicted pressure drop of the lower flow rates provide a predicted pressure drop of less than 2.5 psi. The design is also scalable to accomplish lower pressure drops if desired, by reducing the number of coaxial cylinders in series (e.g., from two to one) as necessary. In another aspect, the design is also scalable to accomplish treatment of concentrated batch-fed media with much lower transmittance (absorbance of about 40 absorbance units) by reducing the gap to 1 mm and employing multiple units operating at 0.5 liters per minute.

EXAMPLE 4

UVC Treatment Apparatus with 3 mm Gap and Tangential Inlet, Connector, and Outlet A lab scale prototype of a UVC reactor, capable of handling high absorbance fluids such as cell culture media at high flow rates to ensure viral inactivation while not exceeding high dosage that may cause media degradation, was built and tested. The testing method was based on a method developed by Bohrerova et al, for UV reactor validation through the use of fluorescent microspheres. See Bohrerova, Z., Bohrer, G., Mohanraj, S. M, Ducoste, J., and Linden, K. G., *Experimental measurements of Fluence distribution in a UV reactor using Fluorescent microspheres*, Environ. Sci. Technol. 39: 8925-8930 (2005). In this method, a distribution of UV dose exposure was obtained through the correlation of fluorescence of microspheres to UV fluence values.

Materials and Methods

Fluorescent microspheres sensitive to UVC exposure (254 nm) were obtained from PolyMicrospheres, Division of Vasmo, Inc., Indianapolis, Ind., which came in a 10 mL solution that was 1 wt % solids, which equated to approximately 4.44×10$^9$ particles/mL. They had a mean diameter of approximately 1.6 μm. These microspheres undergo photobleaching when exposed to UVC radiation proportional to the UV fluence. This dependence enabled utilization of these microspheres in measuring UV dose distributions.

UVC Treatment of Fluorescent Microspheres in Media

Media Preparation

Two days before the experiment, cell culture media (UVC absorbance of about 1.95 absorbance units) and 10% donor bovine serum (DBS) containing cell culture media (UVC absorbance of about 5.3 absorbance units) were taken out of the cold room and allowed to equilibrate at room temperature. To prepare the microsphere spiking solution, 500 mL solutions of cell culture media were mixed with 2 mL microsphere solution, achieving a concentration of about 1.8×10$^7$ microspheres/mL The spiking solution bottles were covered with aluminum foil to prevent pre-experiment exposure.

UVC Prototype Testing

The UVC prototype was built based on the design shown in FIG. 4 with a fluid gap of 3 mm, and an inner and outer cylinder length of about 30" (76 cm). The design consisted of two treatment chambers (1 lamp per chamber) with a tangential inlet and outlet and a tangential connector to maintain and regenerate the swirling cyclonic flow into the chambers. The lamps were low pressure monochromatic lamps at 254 nm with wattage rating of 85 W. However, the UVC efficiency rating was only about 32.9%. The lamps were approximately 29" (73.5 cm) in length. The radiation flux at the quartz surface was estimated as approximately 400 W/m$^2$ based on the quartz surface area and accounting for losses.

Figure 17:
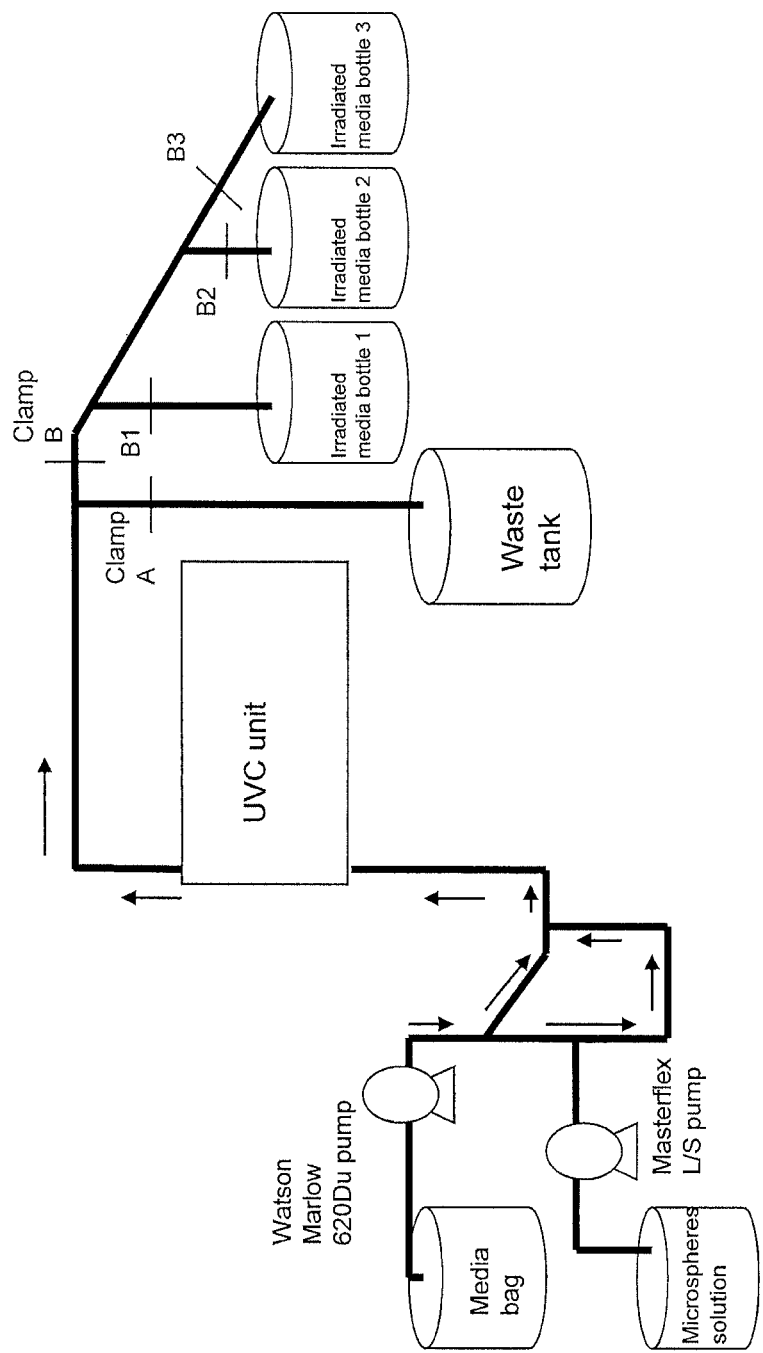
FIG. 17 is a schematic illustration of the UVC treatment setup described in Example 4.

The UVC reactor was set up as per the schematic shown in FIG. 17. The system was flushed with de-ionized water before the media bag was connected.

To reach target mean UV fluences of 40, 58, and 100 mJ/cm$^2$, the necessary flow rates were estimated based on extrapolation of prior CFD predictions as shown in Table 1. A diluted solution of microspheres was spiked into the flow before the media entered the UVC reactor to achieve a concentration of about 1×10⁵ microspheres/mL. These flow rates are also summarized in Table 1.

The UVC reactor had a volume of approximately 650 mL. To achieve a consistent outlet concentration of microspheres, a 99% washout was targeted once microsphere spiking began. Table 1 includes the calculated washout times for each flow rate. Washout times were calculated assuming a well mixed reactor.

The Petri factor and the UV transmittance of the stock microsphere solution were determined prior to sample irradiation. See Bolton, J. R., and Linden, K. G., *Standardization of Methods for Fluence (UV Dose) Determination in Bench-Scale UV Experiments*, J. Environ. Eng., 129(3), 209 (2003). Irradiance measurements were taken immediately before and after sample exposure. Samples were mixed using a micro magnetic stir bar in a 60×15 mm Petri dish with a total volume of 0.32 mL.

TABLE 1

Calculated volumetric flow rates to meet target UV fluences, microsphere spiking flow rates, and washout times for concentration equilibration

| | Target UV Fluence (mJ/cm²) | # of Lamps | Flow Rate (L/min) | Microsphere Spiking Flow Rate (mL/min) | Washout Time (s) |
|---|---|---|---|---|---|
| Cell Culture Media (serum-free) | 40 | 1 | 7.6 | 42.9 | 30 |
| | 58 | 1 | 4.75 | 26.8 | 40 |
| | 100 | 1 | 2.75 | 15.5 | 70 |
| Serum Containing Cell Culture Media (10% DBS in media) | 40 | 2 | 6.0 | 33.9 | 30 |
| | 58 | 2 | 3.8 | 21.5 | 50 |
| | 100 | 2 | 2.2 | 12.4 | 90 |

For all cell culture media runs, flow was directed to the waste tank until the appropriate washout time had been reached, as per Table 1. Flow was then redirected to the irradiated media bottles for three minutes, switching bottles every minute. The system was flushed with de-ionized water between each run.

Control runs for each media type were conducted with both UV lamps turned off, using the same pump settings as those used for a target fluence of 100 mJ/cm². For cell culture media treatment, one of the two UV lamps was disconnected.

For treating the DBS containing media, both lamps were used to achieve target doses. The lamp was turned on for 10 minutes before treatment with de-ionized water running through the UVC unit to prevent overheating. Flow rates were run as per Table 1.

Sampling

After each treatment run, 1 L was poured from each effluent bottle into a 1 L round bottle and the rest was discarded. Round bottles were covered with aluminum foil to prevent further microsphere exposure and stored in the cold room.

On Day 1 of sampling, three 200 μL samples were taken from each cell culture media effluent bottle into a 96-well plate for flow cytometry (FC) analysis. One sample of each untreated media (no microspheres) was also included for comparison purposes.

Day 2 of sampling occurred four days after Day 1 and included two 96-well plates. A sample from each spiking solution was also included, as well as a single sample from each effluent bottle tested Day 1. Plate 2 included a single sample from each effluent bottle of cell culture media.

Bench-Scale Calibration

In order to determine a functional relationship between UV fluence and fluorescence, a bench-scale calibration experiment used a quasi-collimated beam apparatus and a solution of microspheres in water for uniform doses ranging from 10-120 mJ/cm². Samples were run in triplicate in a randomized order, and withdrawn from a stock solution.

Flow Cytometry

The fluorescence change in the microspheres was detected using the BD™ Biosciences special order flow cytometer LSR II, equipped with four lasers. BD Biosciences, San Jose, Calif. The 488 nm blue laser and the 351 nm UV laser were used for excitation of the microspheres. The scattered light was detected with the blue laser and the microspheres' emitted fluorescence light was collected with the UV laser using a band pass filter 407/30 nm. The data was processed and analyzed using the BD™ Biosciences DiVa™ software and/or FlowJo™ (Tree Star, Inc., Ashland Oreg.) data analysis software and also exported to MATLAB for further processing and analysis.

CFD Predictions of UVC Dose

New calculations were performed utilizing the CFD techniques described above at the actual experimental flow-rates and assuming an incident radiation flux from the quartz surface of approximately 400 W/m² to obtain predicted UVC doses. CFD calculations for Vitamin C model solution with absorbance of about 4.7 absorbance units (as described further below) were also conducted to compare with experimental data.

Data Analysis

Preprocessing

Figures 18A, 18B:
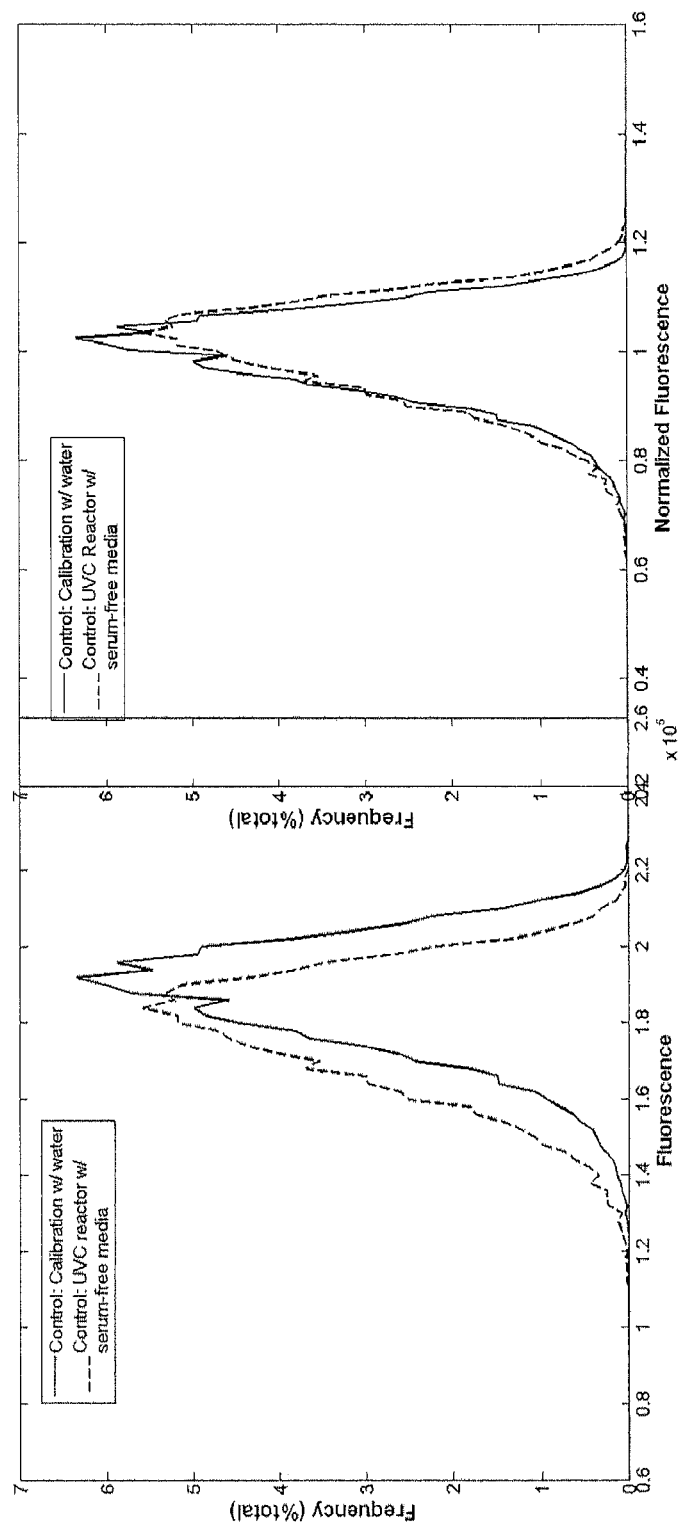
FIGS. 18A and 18B are graphs of fluorescence distributions for controlled samples before (FIG. 18A) and after (FIG. 18B) normalization.

The raw data obtained from flow cytometry was normalized to account for the day to day variability of fluorescence measurements. The means of the fluorescence distribution for respective control samples (0 mJ/cm² UV dose) were chosen as the normalization factor. FIGS. 18A and 18B show the fluorescence distribution for water and cell culture media before (FIG. 18A) and after (FIG. 18B) normalization.

Transforming Fluorescence Distributions into UV Dose Distributions

Figure 19:
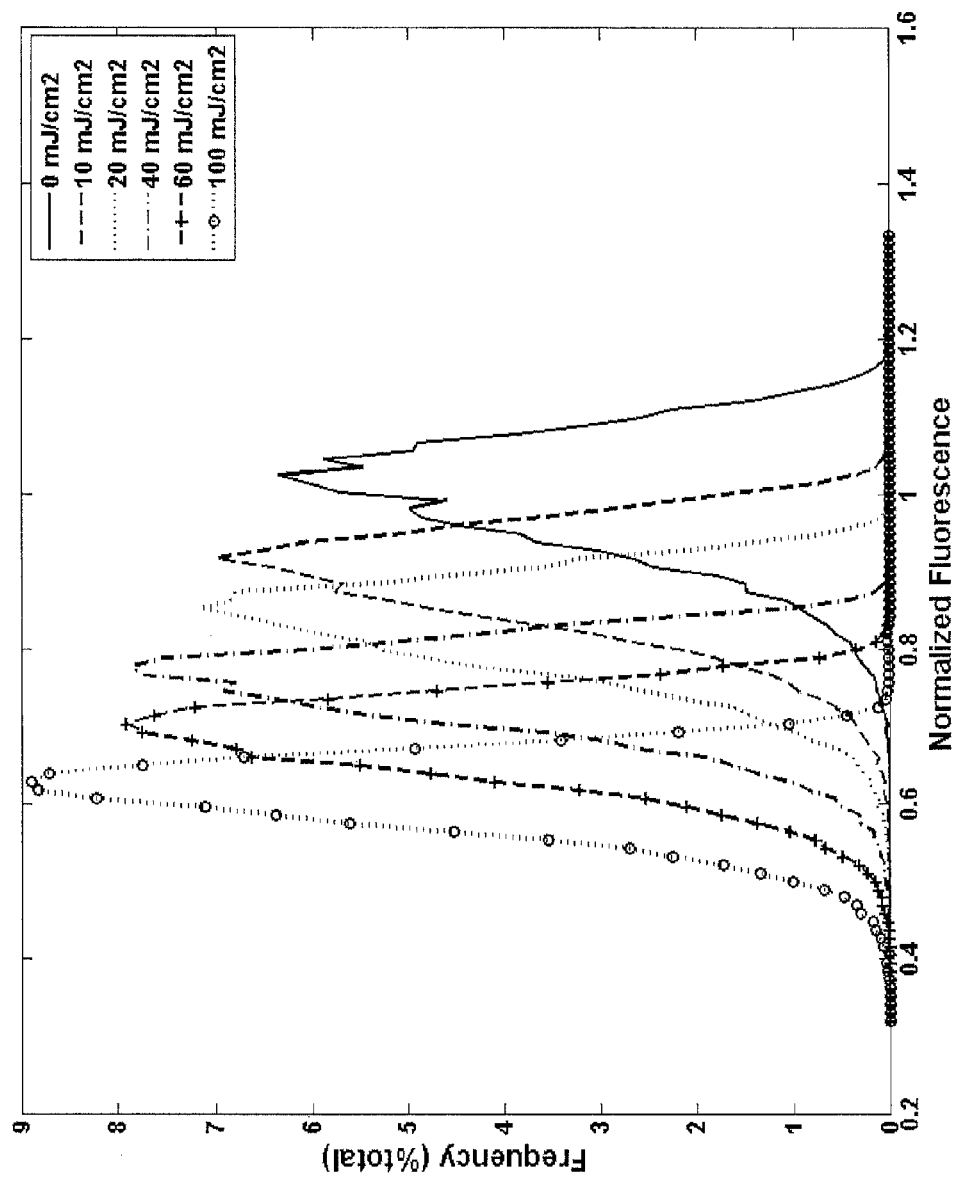
FIG. 19 is a graph of fluorescence distributions at various uniform dose levels obtained from collimated beam calibration experiments.

Fluorescence measurements of samples obtained from calibration experiments showed the distribution of fluorescence for a population of microspheres irradiated at a single UV dose. FIG. 19 shows the fluorescence distributions for samples irradiated at various UV dose levels. Without wishing to be bound by any particular theory, this variation in fluorescence levels is likely attributed to inherent heterogeneity within the microsphere population as well as to characteristics of the flow cytometry equipment.

Figure 20B:
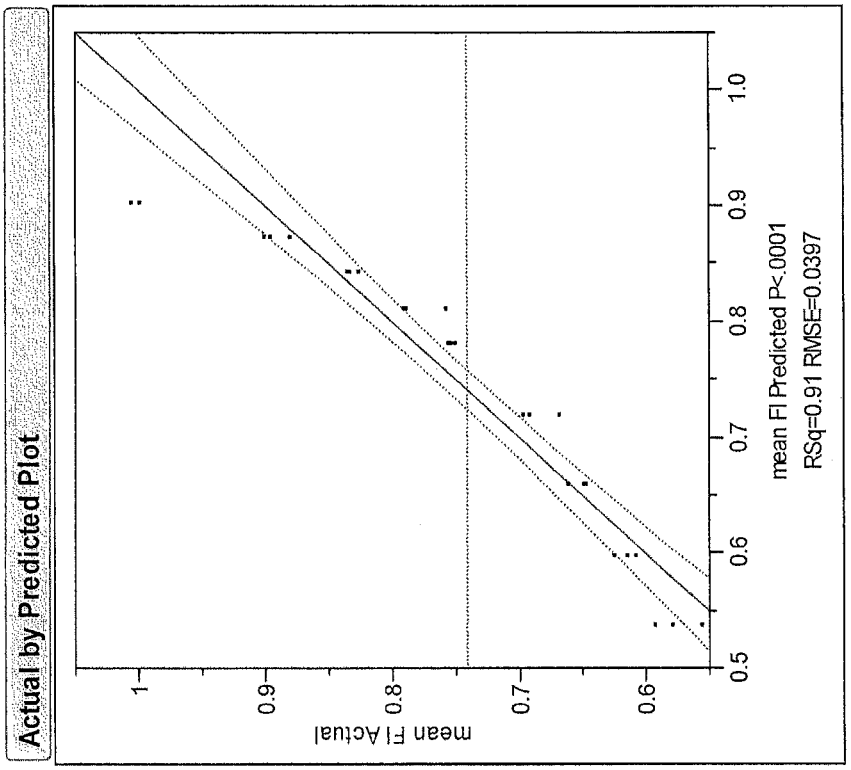
FIGS. 20A and 20B are graphs of means of fluorescence distributions obtained for various UV fluencies from the collimated beam calibration experiments in water.
Figure 20A:
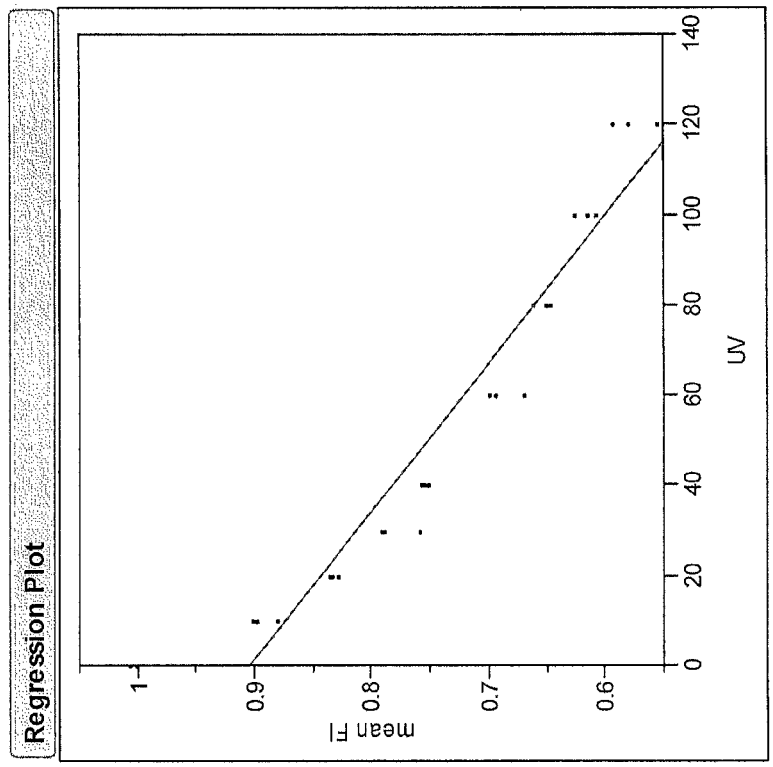

As shown in FIGS. 20A and 20B, based on the literature and scientific predictions, the mean fluorescence of the water calibration data for each UV dose was correlated with a linear fit. The curvature in the fit was primarily at low doses between 0-20 mJ/cm². With the predicted fit shown in FIGS. 20A and 20B, the lower dose results would be over-predicted while higher dose results would be under-predicted with a RMSE of about 12 mJ/cm².

The calibration data was obtained in water, because collimated beam experiments require a uniform dose to particles. In applying the calibration curve to cell culture media or model solutions, such as Vitamin C solutions, the fluorescence data was scaled based on fluorescence readings of microspheres in cell culture media control (UV dose=0) with respect to corresponding fluorescence readings from water control (UV dose=0), to account for the calibration data being collected with water, but being applied to cell culture media.

Figure 21:
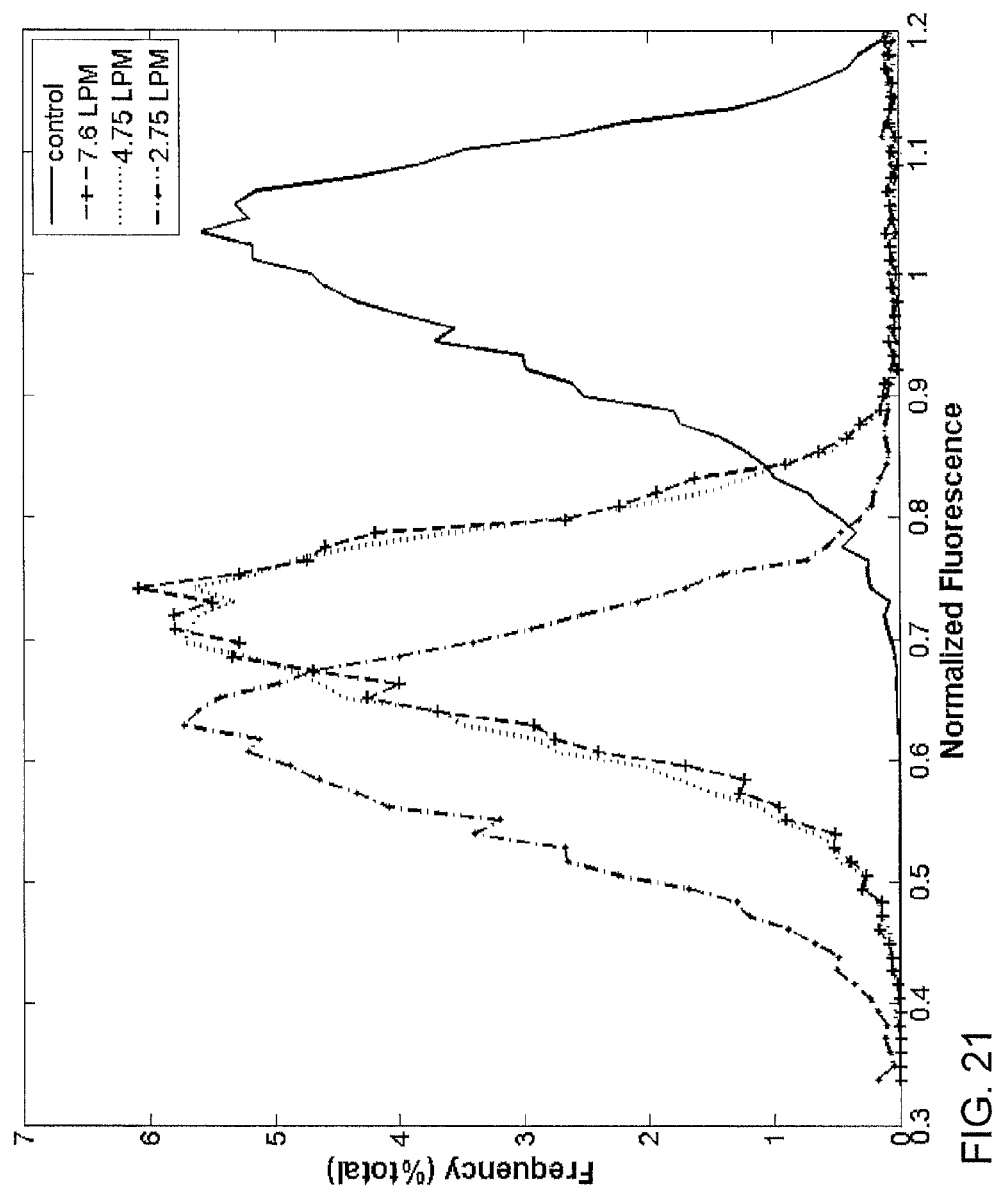
FIG. 21 is a graph of fluorescence distributions of samples exposed to UV light in the UVC reactor at three different flow rates.

Typical fluorescence measurements of samples obtained from UVC reactors for cell culture media at various flow rates are shown in FIG. 21. The goal of the data analysis method was to estimate the dose distribution delivered by the UVC reactor given the fluorescence distribution from flow cytometry measurements. This estimation was performed using a method developed by Blatchley et al., *Dyed microspheres for quantification of UV dose distributions: photochemical reactor characterization by Lagrangian actinometry*, J. Env. Eng. 132: 1390-1403. (2006). These authors, at page 1396, proposed a hypothesis that:

the [fluorescence] distribution in a sample containing microspheres that had been subjected to a distribution of doses was attributable to:
1. UV dose distribution;
2. Measurement errors associated with flow cytometry; and
3. Population heterogeneity among the dyed microspheres. Moreover, it was assumed that these sources of errors were independent, and therefore their effects were additive.

In mathematical terms, it was hypothesized that the [fluorescence] distribution measured in a sample collected from a continuous-flow UV reactor could be represented as the convolution of the [fluorescence] distribution attributable to each individual dose and the dose distribution.

Mathematical Formulations Following Blatchley et al.

Figures 22A, 22B, 22C:
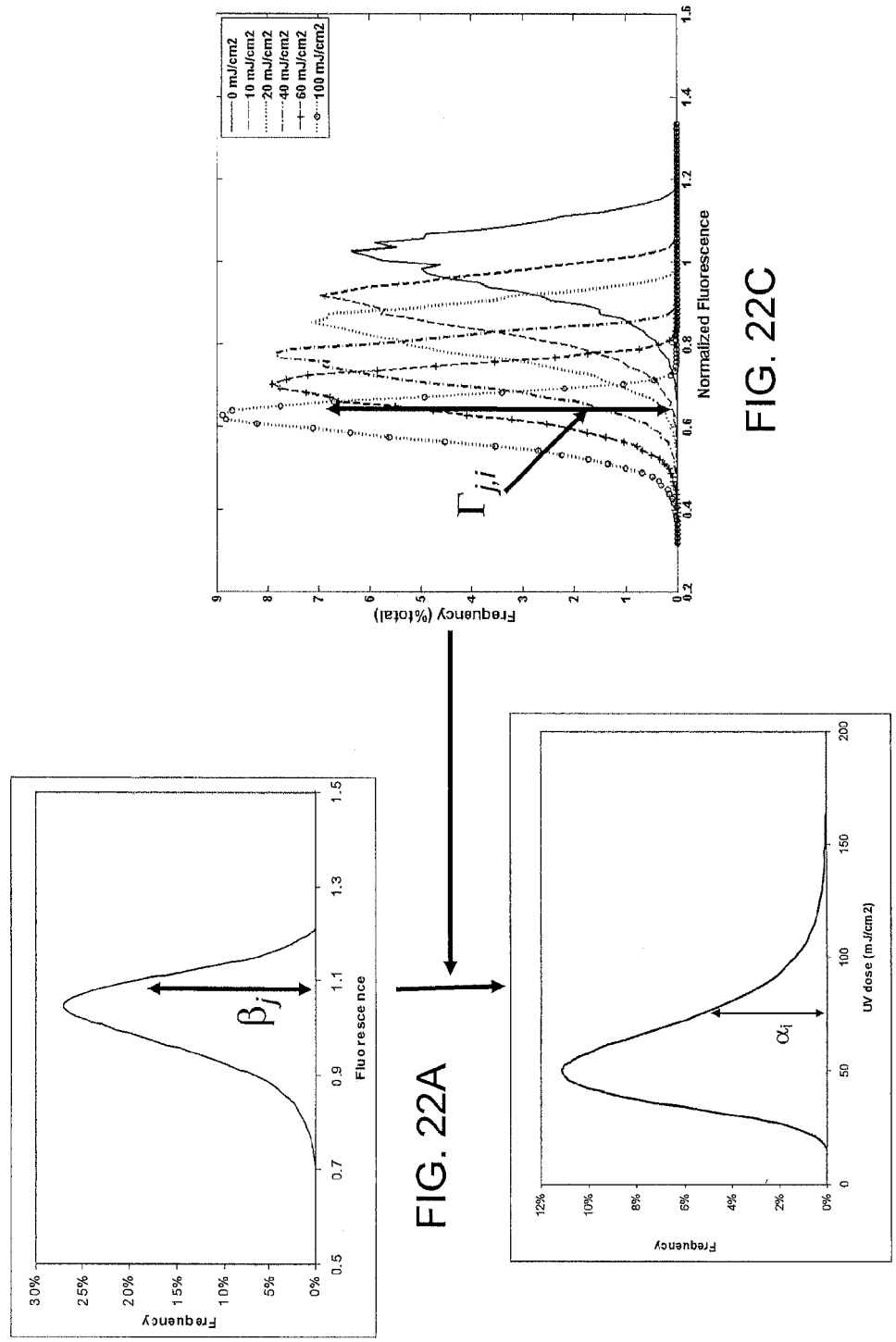
FIGS. 22A, 22B, and 22C are pictorial illustrations of definitions of $\beta_j$, $\Gamma_{j,i}$, and $\alpha_i$.

The following definitions were used during the analysis of data from Example 4, and illustrated pictorially in FIGS. 22A, 22B, and 22C.

i=index for counting dose (D) increments (bin width=5 mJ/cm²; i=1, 2, . . . m)

j=index for founding fluorescence (Fl) increments (bin width=0.02; j=1, 2, . . . n)

$\alpha_i$=fraction of particles in a sample that receive dose $D_i$ $\beta_j$=fraction of particles in a sample that emit florescence $Fl_j$ $\Gamma_{j,i}$=fraction of particles receiving dose $D_i$ that emit fluorescence $Fl_j$ Mathematically, the hypothesis can be represented by following equation—

$$\beta_j = \alpha_0 \Gamma_{j,0} + \alpha_1 \Gamma_{j,1} + \ldots + \alpha_m \Gamma_{j,m} = \sum_{i=0}^{m} \alpha_i \Gamma_{j,i} \quad (2)$$

This equation states that $\beta_j$, the fraction of particles emitting $Fl_j$ is a linear combination of fractions emitting $Fl_j$ due to exposure to various UV doses ranging from $\alpha_0$ to $\alpha_m$. Equation 2, when written for various values of j, forms a set of linear equations which can be represented in vector form as follows—

$$\begin{bmatrix} \beta_0 \\ \beta_1 \\ \ldots \\ \ldots \\ \beta_n \end{bmatrix} = \begin{bmatrix} \Gamma_{0,0} & \Gamma_{0,1} & \ldots & \ldots & \Gamma_{0,m} \\ \Gamma_{1,0} & \Gamma_{1,1} & \ldots & \ldots & \Gamma_{1,m} \\ \ldots & \ldots & \ldots & \ldots & \ldots \\ \ldots & \ldots & \ldots & \ldots & \ldots \\ \Gamma_{n,0} & \Gamma_{n,1} & \ldots & \ldots & \Gamma_{n,m} \end{bmatrix} \times \begin{bmatrix} \alpha_0 \\ \alpha_1 \\ \ldots \\ \ldots \\ \alpha_m \end{bmatrix} \quad (3)$$

$$[\beta] = [\Gamma] \times [\alpha]. \quad (4)$$

The objective of the deconvolution was to yield an estimate of the dose distribution, which was represented by the vector $[\alpha]$. For each operating condition, the vector $[\beta]$ was the fluorescence distribution (histogram) from the flow cytometry analysis of a sample from the UVC reactor.

Approach to Solving Blatchley et al. Equations

The matrix $[\Gamma]$ was calculated by application of the interpolation algorithm using Weibull distribution to the data from the flow cytometry analysis of samples exposed to uniform UV doses during calibration experiments.

To solve the system of equations, it was also assumed that the UV dose distributions (values of $\alpha_i$) follow log normal distribution, based on the expected shape of the UVC dose distribution.

Equation 4 was solved in an iterative fashion as follows:

1) Two parameters of log normal distribution, mean μ and standard deviation σ, were assumed to generate an initial guess for UV dose distribution, $[\alpha]_g$ 2) Fluorescence distribution, $[\beta]_g$, was calculated for given $[\alpha]_g$ using equation 4.

3) Calculated $[\beta]_g$ values were compared with experimentally obtained $[\beta]$ values. Total error was calculated as $$\sum_{j=0}^{n} (\beta_{jg} - \beta_j)^2.$$

4) Value of mean and standard deviation of $[\alpha]_g$ was optimized to minimize the total error. Step 1-3 were repeated until the error was less than a tolerance criteria.

Steps 1-4 were implemented using a MATLAB code (MathWorks, Natick, Mass.).

Verification of Data Analysis Technique

Figure 23:
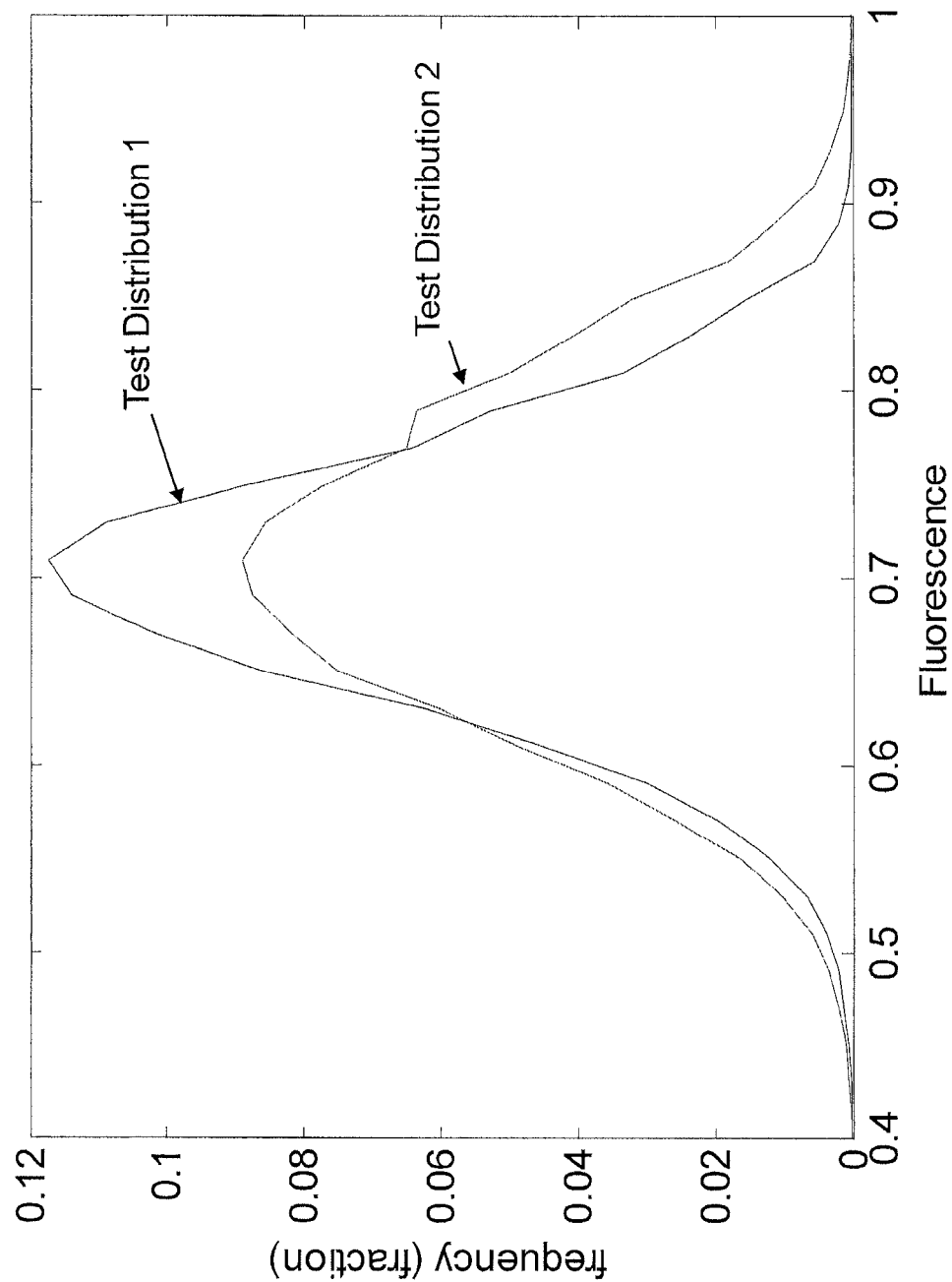
FIG. 23 is a graph of two test fluorescence distributions obtained by mathematically mixing calibration samples in proportions given in Table 2.

The data analysis technique described in the previous section was verified using a mathematical convolution experiment. Test UV distributions were mathematically constructed from the fluorescence measurements for the calibration samples. Fluorescence distribution measurements for calibration samples were mathematically mixed in predetermined proportions to generate new convoluted fluorescence distributions. Two test distributions were generated by mixing calibration samples in proportions shown in Table 2. The resulting fluorescence distribution is shown in FIG. 23.

TABLE 2

Mixing proportions for two test distributions.

| UV dose mJ/cm$^2$ | Test dist 1 multiplier | Test dist 2 multiplier |
|---|---|---|
| 0 | 0 | 0 |
| 10 | 0 | 0 |
| 20 | 0 | 1 |
| 30 | 1 | 3 |
| 40 | 4 | 4 |
| 60 | 10 | 6 |
| 80 | 4 | 3 |
| 100 | 1 | 2 |
| 120 | 0 | 1 |

Figure 24:
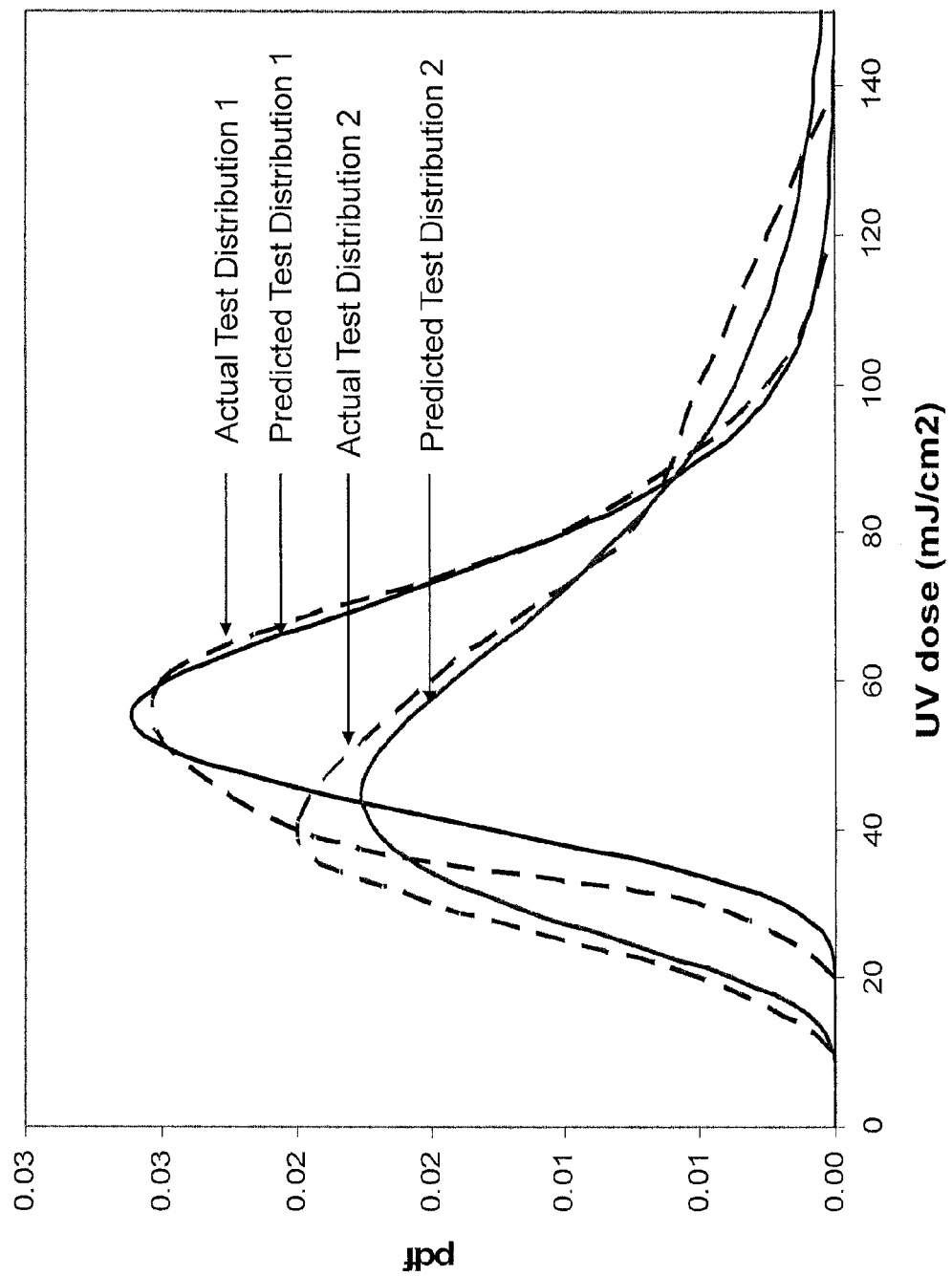
FIG. 24 is a graph of a comparison of the actual and predicted UV dose distributions for the two test cases.

The mathematical technique described in the previous section was applied for calculating UV dose distribution from the fluorescence distributions shown in FIG. 23. Results are shown in FIG. 24. The actual UV dose distributions corresponding to the mixing proportions listed in Table 2 were plotted on the same plot with predicted UV dose distributions. A very good agreement was observed between the actual and the predicted values. FIG. 24 confirmed that the mathematical technique used in this work was capable of predicting UV dose distributions from fluorescence distribution data.

Results

Figures 2, 25A:
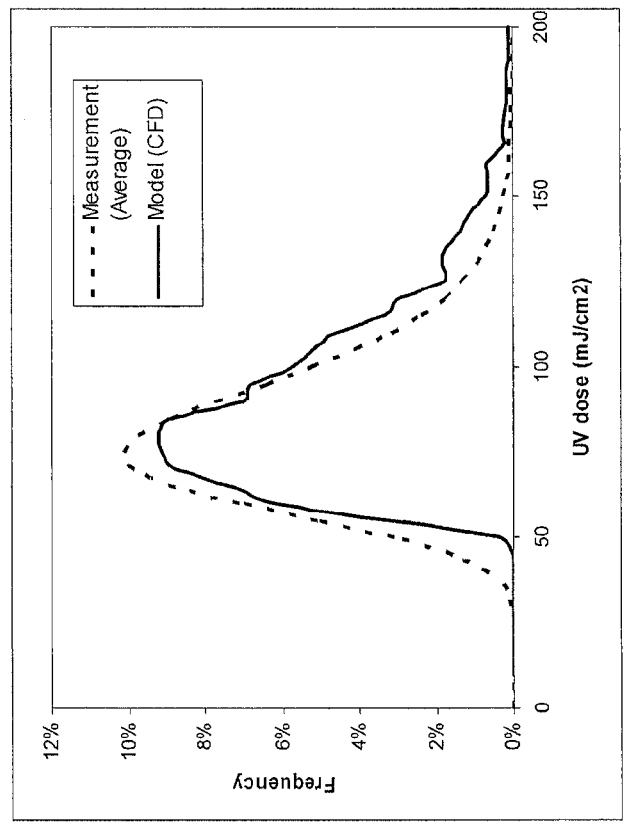
Figures 1, 25A:
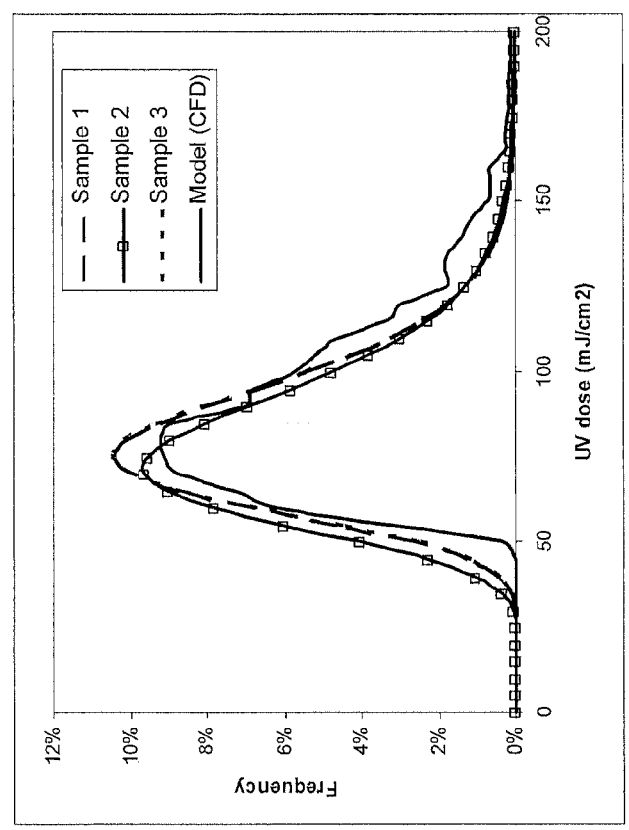
Figures 2, 25B:
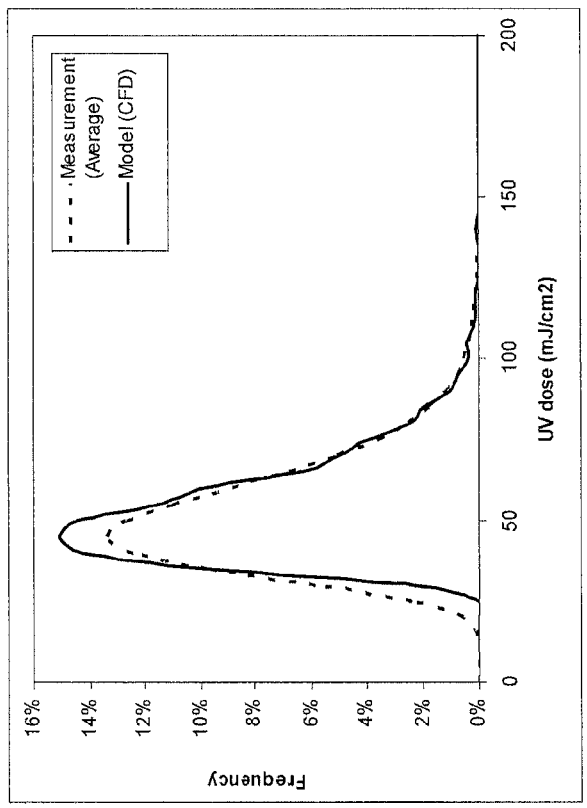
Figures 1, 25B:
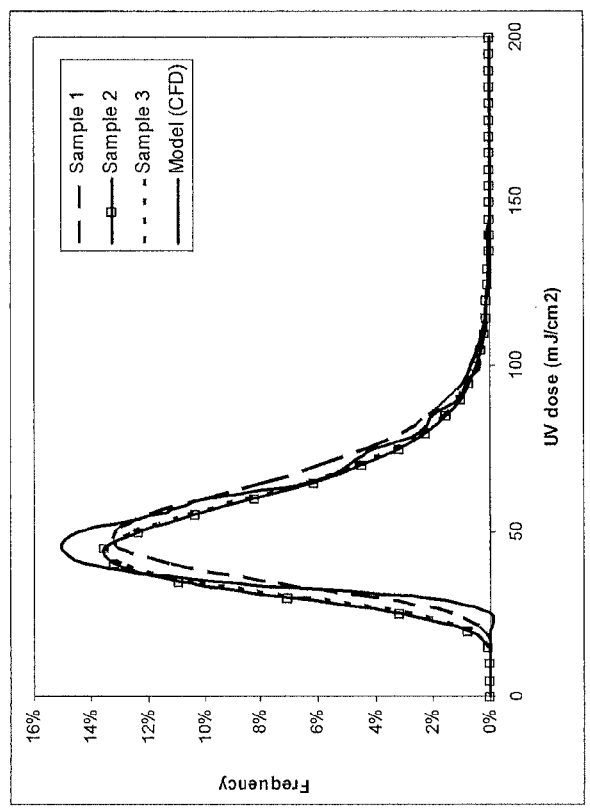
Figures 2, 25C:
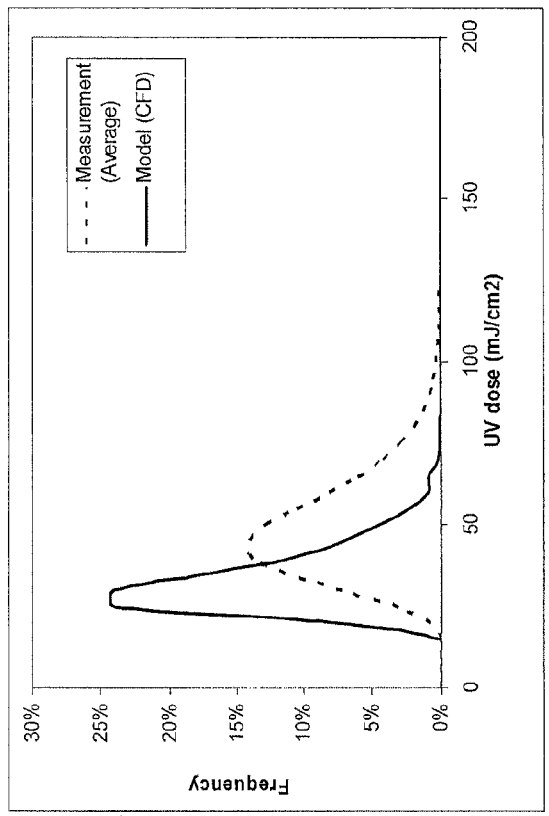
Figures 1, 25C:
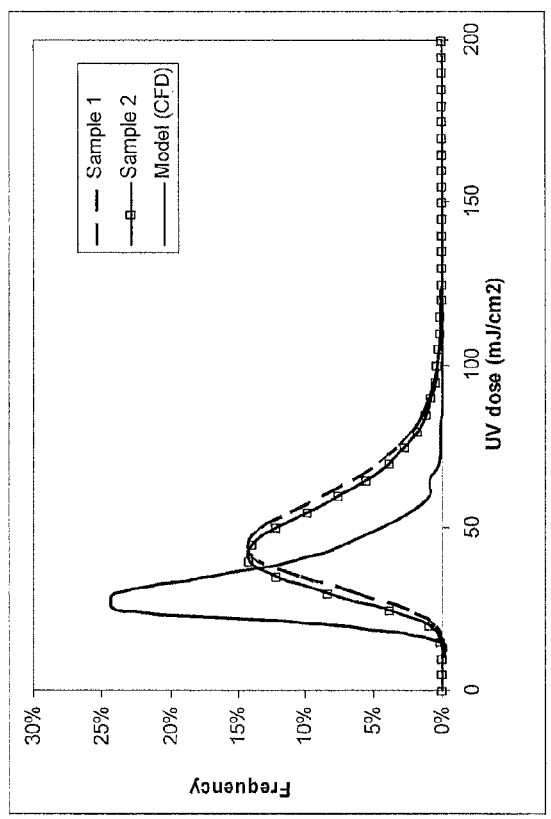

The UV dose distributions of cell culture media through the device estimated from Fl distribution data are shown in FIGS. 25A, 25B, and 25C. The graph for each flow rate shows three different curves obtained from samples collected in three different jars, representing different time points in the processes. Minimal variation from jar to jar indicated steady operation of the UVC reactor. UV dose distribution predicted by CFD simulation was also plotted on the same plot. The CFD calculations for the exact experimental conditions were used to compare to the experimental results.

At a high flow-rate of 7.6 liters per minute (LPM), it is believed that there were pumping problems with maintaining uniform flow during the experiment, and therefore the third sample did not receive enough microspheres for flow cytometry analysis, as shown in FIG. 25C-1. The results were also over-predicted at the high flow-rate, which was consistent with the quality of the fit shown in FIGS. 20A and 20B.

Figures 1, 26A:
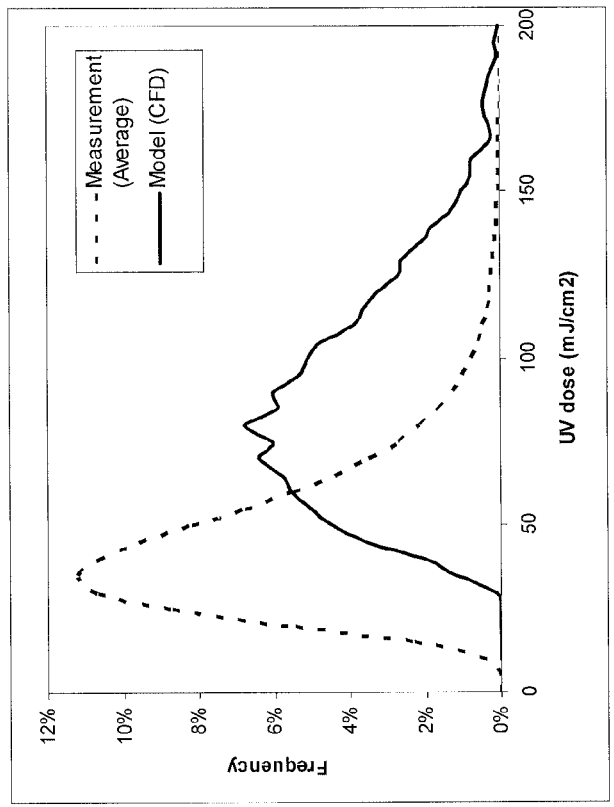
Figures 2, 26A:
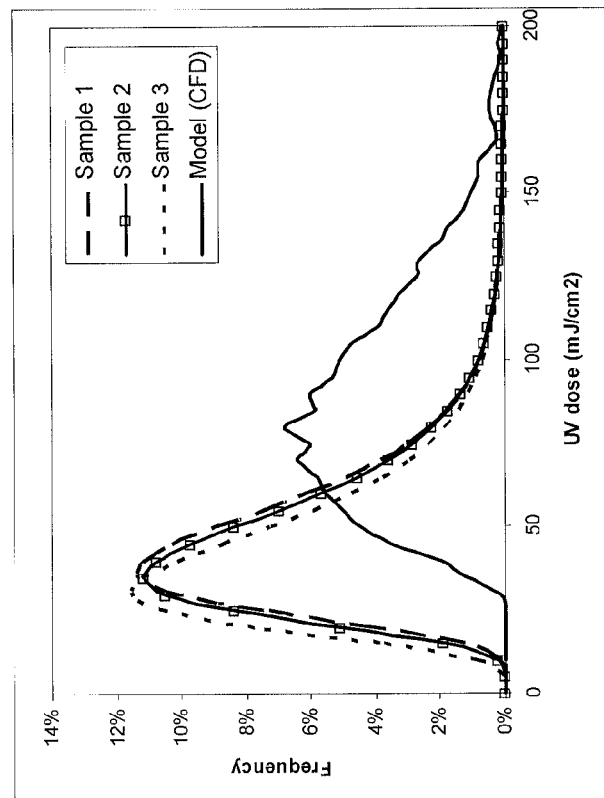
Figures 1, 2, 26B:
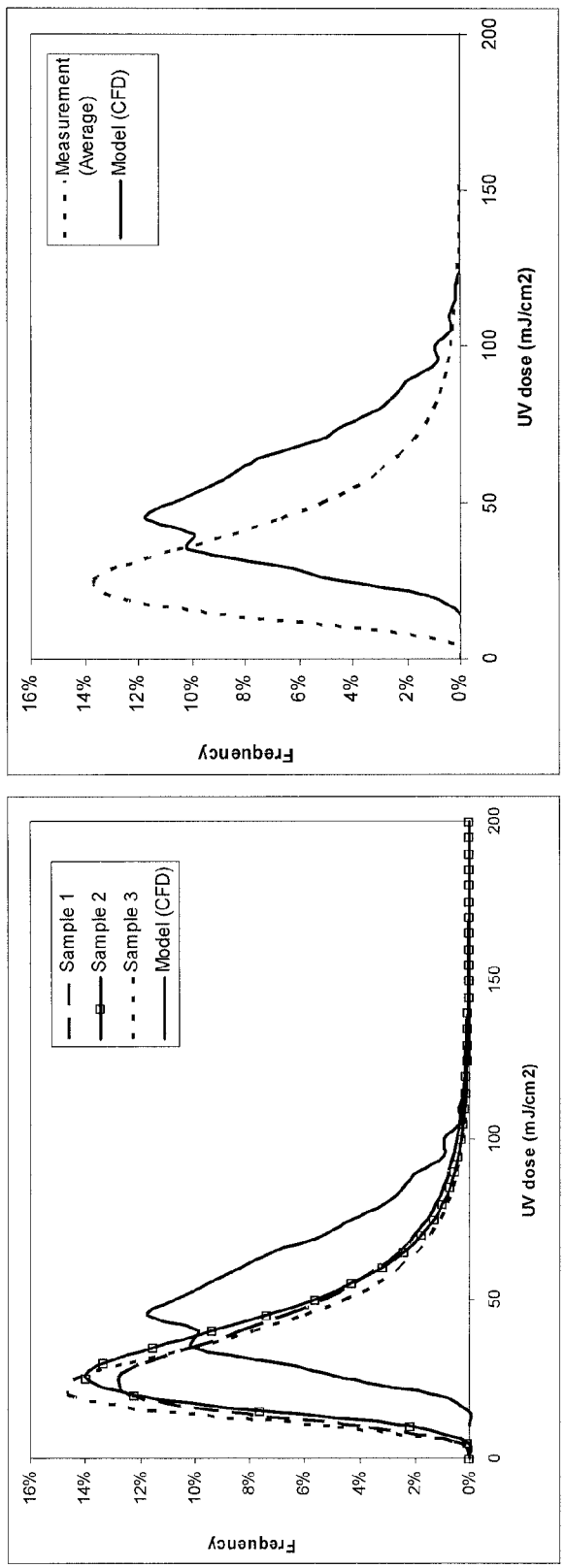
Figures 1, 2, 26C:
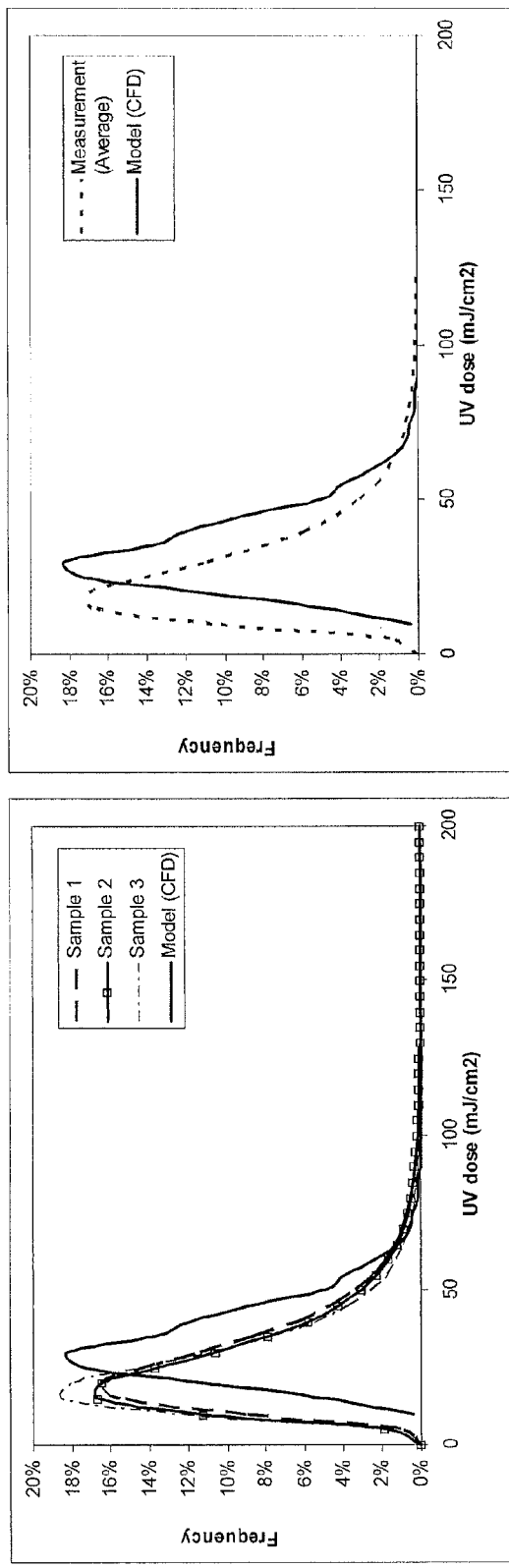

The UV dose distributions of 10% DBS in cell culture media through the device estimated from Fl distribution data and compared with model (CFD) as shown in FIGS. 26A, 26B, and 26C. The observation from serum containing media was consistent under prediction of expected UV dose distribution including the mean values.

Figure 27:
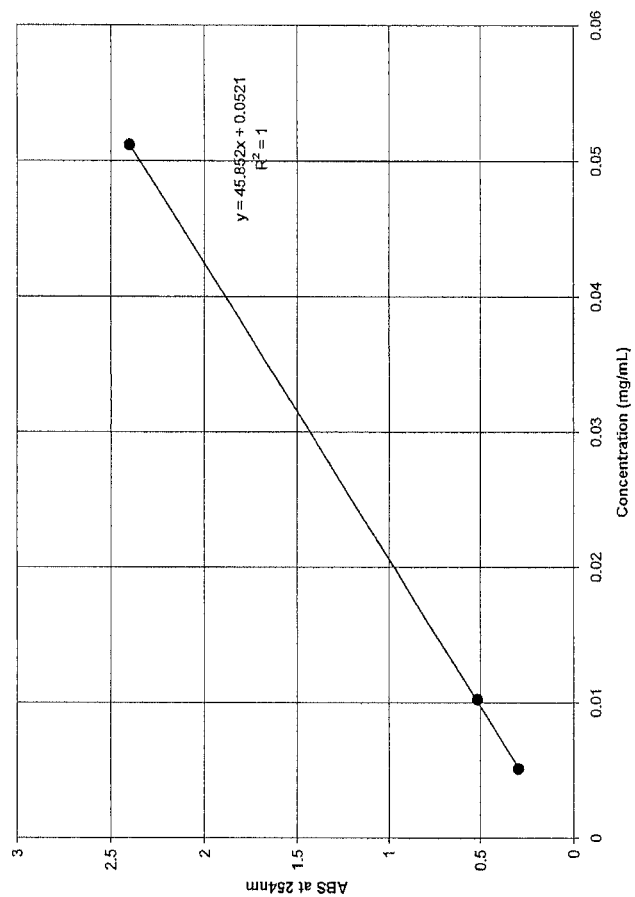
FIG. 27 is a graph of UVC absorbance measurements of Vitamin C solution in water.

Since the physics of flow and UVC radiation was not expected to change in the range of flow-rates and absorbances studied, the observation that all the experimental UV mean doses were consistently lower than predicted was potentially due to interaction of microspheres with serum components in the 10% DBS media, causing a shielding effect and confounding the results. A model solution that has similar absorbance as 10% DBS cell culture media was used to resolve this potential discrepancy in the results. Vitamin C solution in water was identified as a potential candidate for such a model solution. Vitamin C (Ascorbic acid) solutions at 3 different concentrations were tested using a UV-Spectrophotometer (Agilent 8453) to measure absorbance at 254 nm. The results, as shown in FIG. 27, confirmed that Vitamin C solution can be used as a model fluid to mimic the absorbance of 10% DBS cell culture media, while maintaining a water-like viscosity and density.

A stock solution of 10 g/L of Vitamin C solution was used to make a 0.1 g/L Vitamin C solution which had a UVC absorbance of about 4.7 absorbance units. Absorbance values were measured prior to and after the experiment with UV irradiation to confirm that the absorbance of the solution did not change due to UV exposure. The experimental procedure employed with the model solution was identical to that of conducting the cell culture irradiation experiments.

Figures 1, 2, 28A:
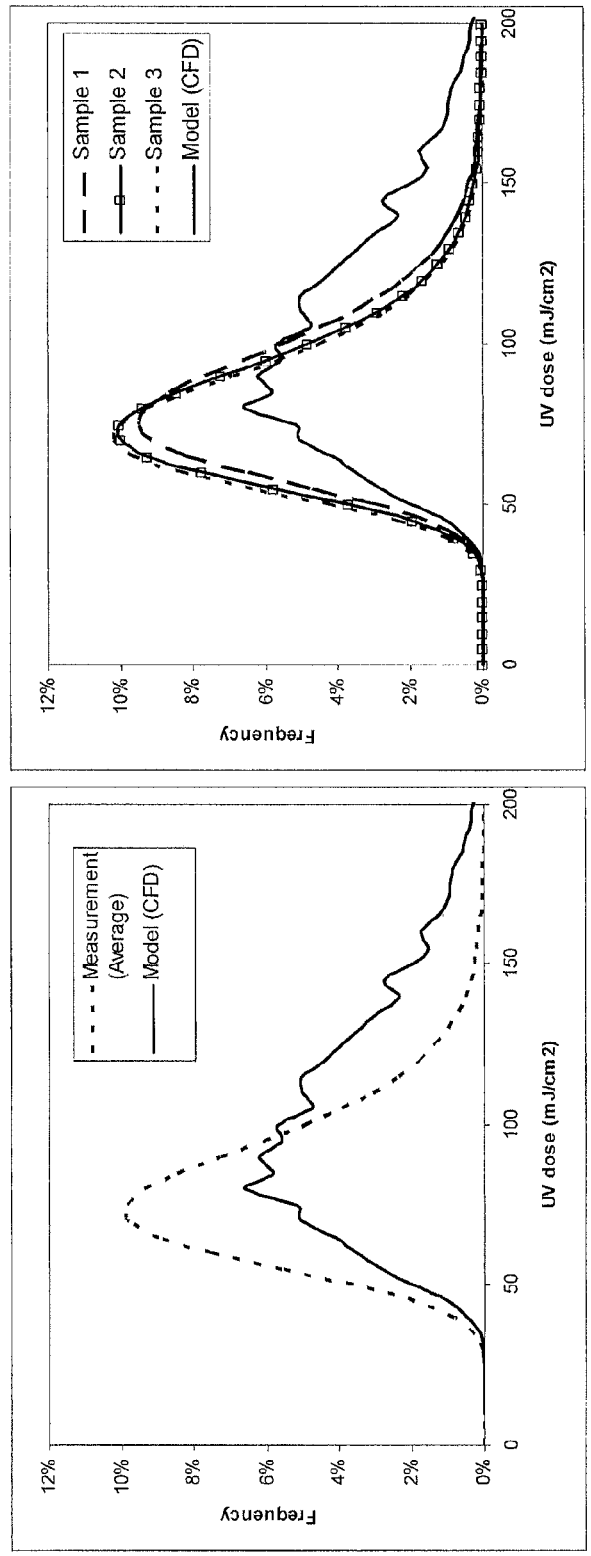
Figures 2, 28B:
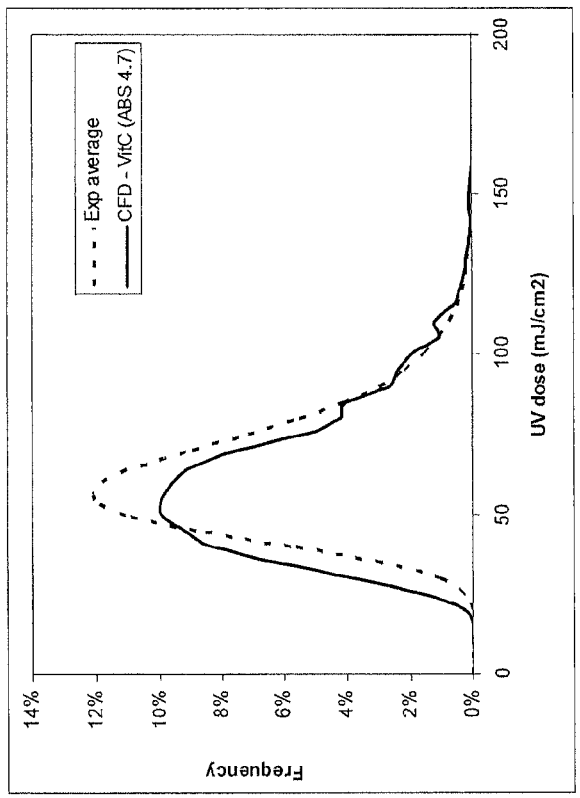
Figures 1, 28B:
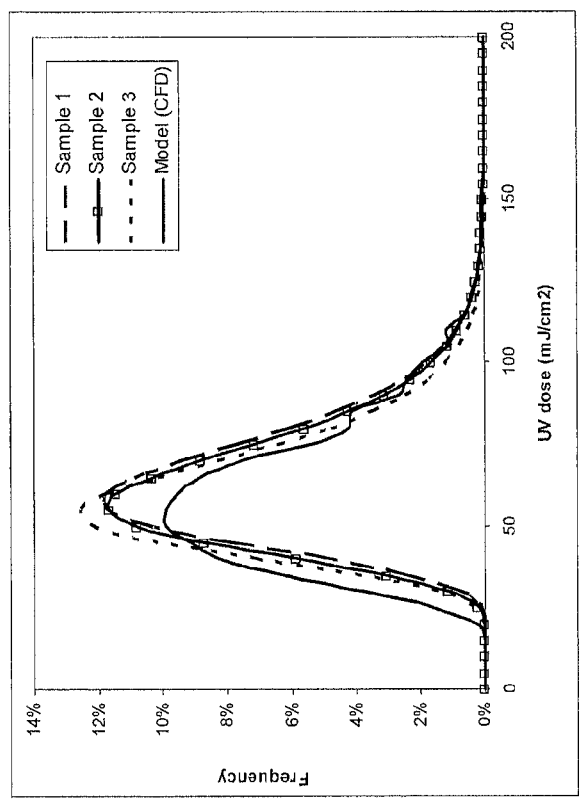

The results from 0.1 g/L Vitamin C solution were compared with CFD predictions for absorbance values of 4.7 and shown in FIGS. 28A and 28B. With the Vitamin C model solution, the model results agreed well with experimental results confirming that the device functions well even with high absorbance fluids, such as serum-containing cell culture media.

The experiments were also repeated with Vitamin C solution to mimic serum-free cell culture media (absorbance of 1.95 absorbance units). A concentration of 0.04 g/L of Vitamin C solution provided a UVC absorbance of 1.94 absorbance units, and this was confirmed by sampling the solution prior to UV treatment. A sample of the irradiated solution was also taken for UVC absorbance measurement to confirm that the absorbance of the solution did not change due to irradiation. The experimental procedure employed with the model solution was identical to that of conducting the cell culture irradiation experiments. The results from the 0.04 g/L Vitamin C solution are compared with CFD predictions and shown in FIGS. 29A, 29B, and 29C.

Figures 2, 29A:
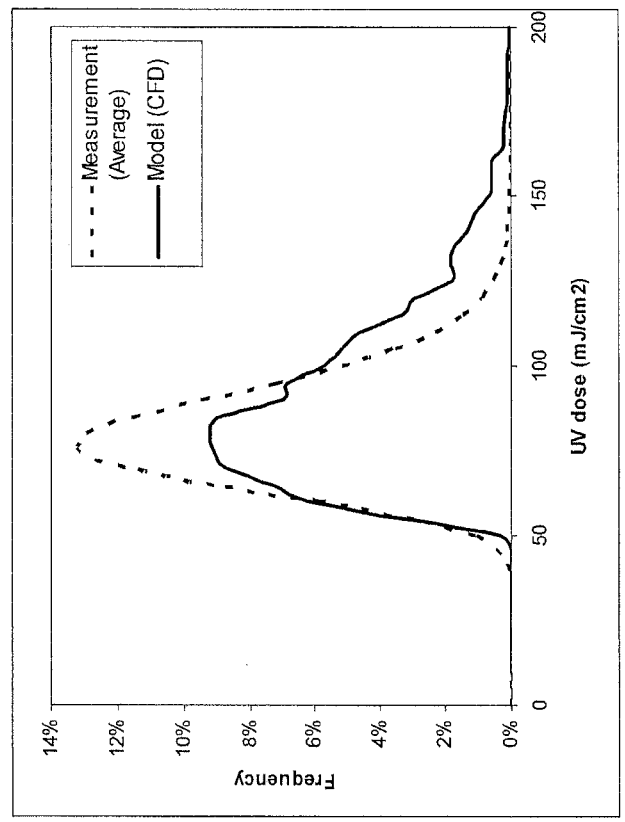
Figures 1, 29A:
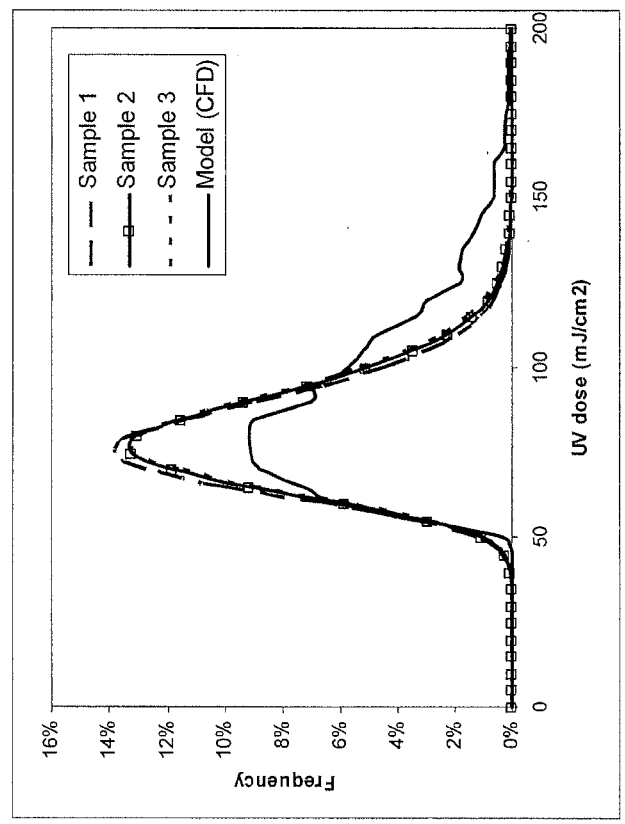
Figures 2, 29B:
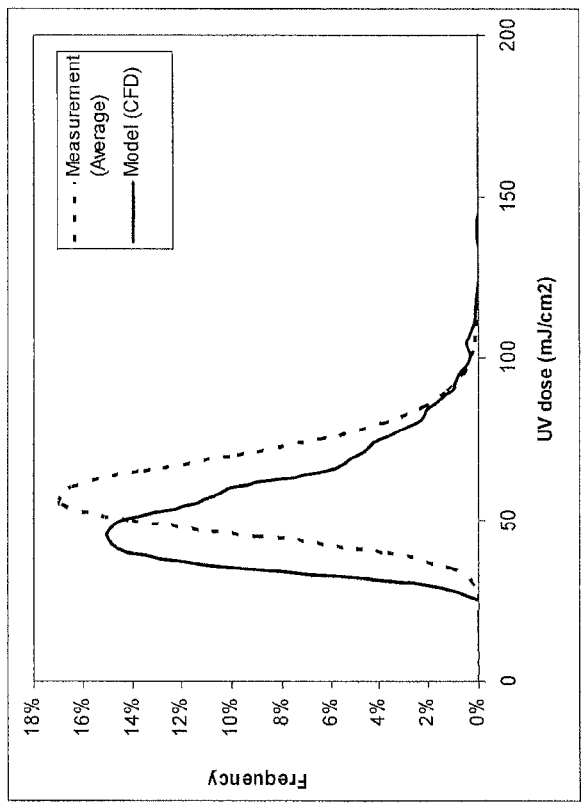
Figures 1, 29B:
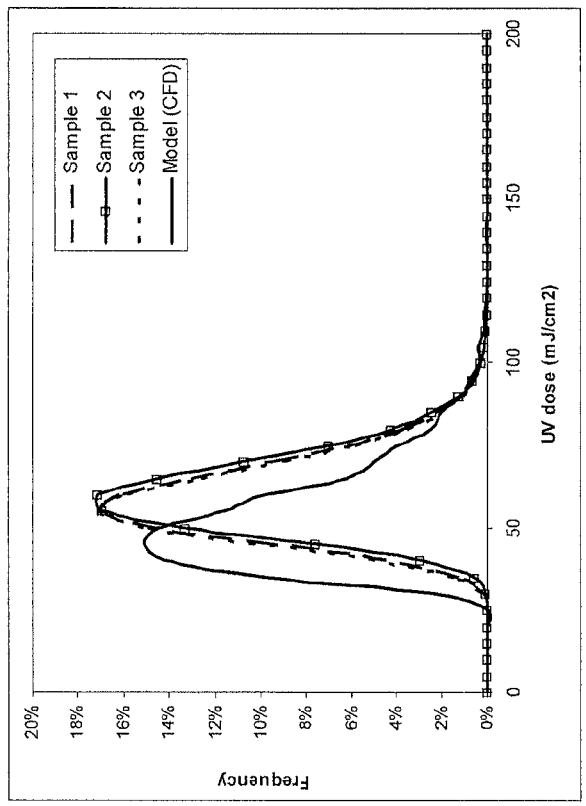
Figures 2, 29C:
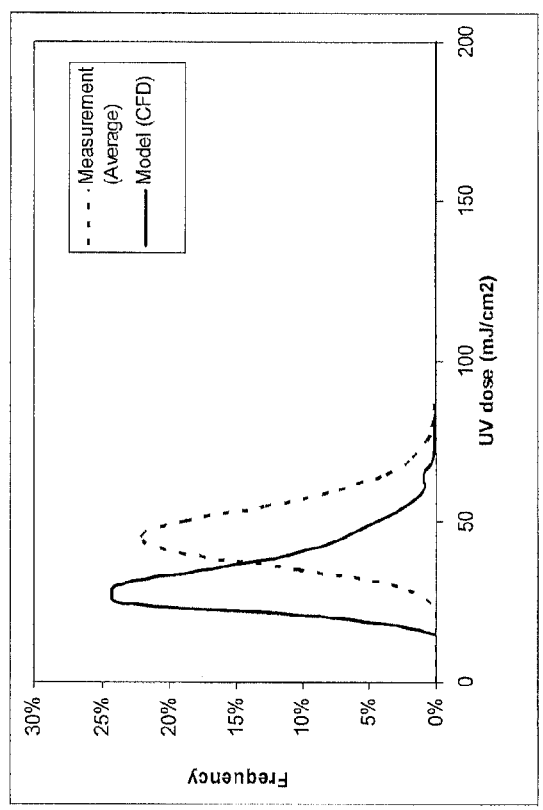
Figures 1, 29C:
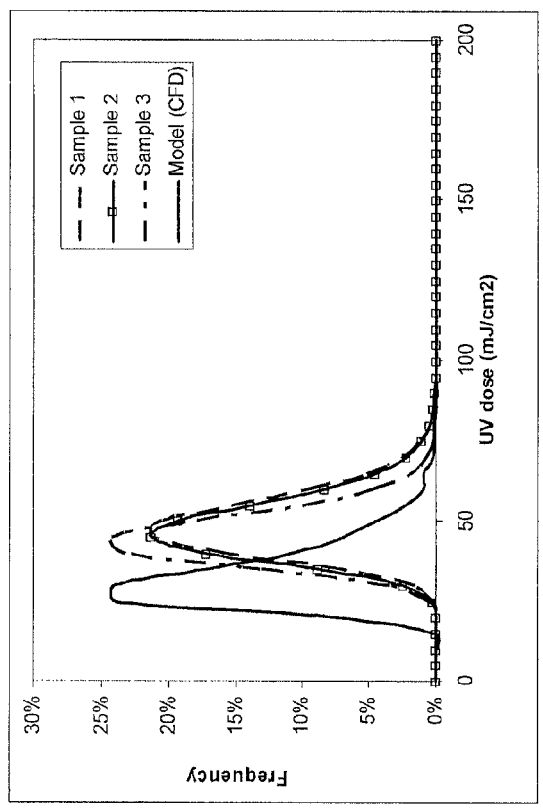

The Vitamin C model solution produced similar results to serum-free cell culture media, as demonstrated by comparing FIGS. 25A, 25B, and 25C with FIGS. 29A, 29B, and 29C, providing confirmation of the approach taken with Vitamin C as a model solution. The variability observed was within experimental variability and quality of the fit with water calibration data and the approximations used to extend the water calibration dataset to high absorbance fluids such as cell culture media.

Conclusions

A lab scale prototype built based on the design shown in FIG. 4 was tested with the use of fluorescent microspheres to measure UVC dose distributions with cell culture media. The unit had a 3 mm flow gap with tangential inlet, outlet and also a tangential connector for 2 treatment chambers. Results showed that experimentally measured UV dose distributions matched closely with CFD model predictions. Serum-containing cell culture media results under-predicted the dose, which may be due to interactions of serum components with fluorescent microspheres confounding the results. The experiments were repeated with vitamin C solution in water as a model fluid for serum-containing cell culture media, since this provided similarly high absorbance values. The results showed good agreement with CFD predictions, demonstrating that the prototype was able to deliver UV doses capable of viral inactivation in high absorbance liquids. The model fluid with Vitamin C as a valid approach was verified by creating model Vitamin C solutions for serum-free cell culture media, and the results confirmed good agreement with the predictions.

In summary, it was demonstrated that the apparatus of the invention, as illustrated by the UVC prototype unit, was capable of producing narrow UVC dose distributions, as predicted, for high absorbance fluids such as cell culture media with or without serum. Accordingly, the apparatus of the invention delivers UVC doses required to kill a variety of viruses.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A high throughput apparatus for viral inactivation of a high absorbance liquid comprising:
   a) a first coaxial cylinder and at least one second coaxial cylinder connected in series, each coaxial cylinder comprising:
      i) an outer cylinder having a length, an inner diameter, an outer diameter, and an inner wall;
      ii) an inner cylinder coaxial with the outer cylinder, having a length substantially equal to the length of the outer cylinder and having an outer diameter adapted to form a gap between the outer diameter of the inner cylinder and the inner diameter of the outer cylinder, wherein the gap is in a range between 1 mm and 5 mm;
      iii) an inlet associated with the outer cylinder and configured to flow the liquid along the gap in a substantially cyclonic flow path, wherein the inlet is located such that a center line along the inlet intersects a radius of the associated outer cylinder perpendicular to the center line along the inlet at a location at, or proximal to the outer diameter of the associated outer cylinder, and wherein the inlet has an inner wall extending from the inner wall of the associated outer cylinder;
      iv) at least one emitter of type C ultraviolet radiation placed inside the inner cylinder so as to emit the type C ultraviolet radiation towards the liquid, thereby, in conjunction with the substantially cyclonic flow of the liquid, producing a narrow dose distribution of type C ultraviolet radiation that inactivates or kills viruses in the liquid;
      v) an outlet connected to the outer cylinder opposite the inlet; and
   b) a connector having a first end in fluid communication with the outlet of the first coaxial cylinder and a second end in fluid communication with the inlet of a first of the at least one second coaxial cylinder to form a series of coaxial cylinders, the connector extending from the inlet of the second coaxial cylinder tangential to the outer cylinder of the first of the at least one second coaxial cylinder.

2. The apparatus of claim 1, wherein a line parallel to the center line along at least one of the inlets forms an axial angle with the axis of the associated outer cylinder and a radial angle with the radius of the associated outer cylinder.

3. The apparatus of claim 2, wherein at least one of the inlets is tangential to the associated outer cylinder.

4. The apparatus of claim 2, wherein the axial angle is in a range of between about 30 degrees and about 90 degrees.

5. The apparatus of claim 2, wherein the radial angle is in a range of between about 90 degrees and about 150 degrees.

6. The apparatus of claim 1, wherein at least one of the emitters of type C ultraviolet radiation emits radiation of a wavelength in a range of between about 240 nm and about 260 nm.

7. The apparatus of claim 1, wherein the inner cylinders are made of a material selected from the group consisting of fluoropolymer and quartz.

8. The apparatus of claim 1, wherein the gap of at least one of the coaxial cylinders includes static mixing elements.

9. The apparatus of claim 1, wherein least one of the outlets is configured to create or maintain the cyclonic flow of the cell culture media upon exit.

10. The apparatus of claim 1, further including an input manifold and an output manifold, and wherein the series of coaxial cylinders includes a first series of coaxial cylinders and a second series of coaxial cylinders, each of the series of coaxial cylinders having an inlet in fluid communication with the input manifold and an outlet in fluid communication with the output manifold.

11. The apparatus of claim 1, wherein the connector includes static mixer elements.

12. The apparatus of claim 1, wherein the lengths of the outer cylinders and the inner cylinders are in a range of between about 25 cm and about 100 cm.

13. The apparatus of claim 1, wherein the number of emitters of type C ultraviolet radiation is in a range of between 2 and 8 emitters.

14. The apparatus of claim 1, wherein the gap of at least one of the coaxial cylinders includes flow deflectors.

15. The apparatus of claim 1, further including one or more of the following: a monitor which indicates dosage of radiation to which the cell culture media has been exposed, a shut-off valve to turn off the flow of cell culture media, a flushing system to flush out cell culture media that has been over-exposed or under-exposed to radiation, or a pump.

16. A method of inactivating viruses in cell culture media using the apparatus of claim 1 comprising:

a)introducing cell culture media through the inlet of the first coaxial cylinder;

b) flowing the cell culture media through the gaps of the first coaxial cylinder and the at least one second coaxial cylinder in a substantially cyclonic flow path along the gaps;

c) irradiating the cell culture media with the emitters of type C ultraviolet radiation placed inside the inner cylinders so as to emit the type C ultraviolet radiation towards the cell culture media to thereby inactivate viruses in the cell culture media; and d) flowing the cell culture media through the outlet of the at least one second coaxial cylinder; and e) flowing the cell culture media through the connector.

17. The method of claim 16, wherein the cell culture media flows at a flow rate in a range of between about 0.5 liters per minute and about 50 liters per minute.

18. The method of claim 16, wherein a line parallel to the center line along at least one of the inlets forms an axial angle with the axis of the associated outer cylinder and a radial angle with the radius of the associated outer cylinder.

19. The method of claim 18, wherein at least one of the inlets is tangential to the associated outer cylinder.

20. The method of claim 18, wherein the axial angle is in a range of between about 30 degrees and about 90 degrees.

21. The method of claim 18, wherein the radial angle is in a range of between about 90 degrees and about 150 degrees.

22. The method of claim 16, wherein the dose of radiation delivered by the emitters of type C ultraviolet radiation to the cell culture media is in a range of between about 5 $mJ/cm^2$ and about 100 $mJ/cm^2$.

23. The method of claim 16, wherein at least one of the emitters of type C ultraviolet radiation emits radiation of a wavelength in a range of between about 240 nm and about 260 nm.

24. The method of claim 16, wherein the inner cylinders are made of a material selected from the group consisting of fluoropolymer and quartz.

25. The method of claim 16, wherein the gap of at least one of the coaxial cylinders includes static mixing elements.

26. The method of claim 16, wherein least one of the outlets is configured to create or maintain the cyclonic flow of the cell culture media upon exit.

27. The method of claim 16, further including an input manifold and an output manifold, and wherein the series of coaxial cylinders includes a first series of coaxial cylinders and a second series of coaxial cylinders, each of the series of coaxial cylinders having an inlet in fluid communication with the input manifold and an outlet in fluid communication with the output manifold.

28. The method of claim 16, wherein the connector includes static mixer elements.

29. The method of claim 16, wherein wherein the lengths of the outer cylinders and the inner cylinders are in a range of between about 25 cm and about 100 cm.

30. The method of claim 16, wherein the number of emitters of type C ultraviolet radiation is in a range of between 2 and 8 emitters.

31. The method of claim 16, wherein the gap of at least one of the coaxial cylinders includes flow deflectors.

32. The method of claim 16, further including one or more of the following: a monitor which indicates dosage of radiation to which the cell culture media has been exposed, a shut-off valve to turn off the flow of cell culture media, a flushing system to flush out cell culture media that has been over-exposed or under-exposed to radiation, or a pump.

* * * * *